United States Patent
Angle et al.

(10) Patent No.: US 10,653,330 B2
(45) Date of Patent: May 19, 2020

(54) SYSTEM AND METHODS FOR PROCESSING NEURAL SIGNALS

(71) Applicant: PARADROMICS, INC., Austin, TX (US)

(72) Inventors: Matthew Angle, Austin, TX (US); Edmund Huber, San Francisco, CA (US); Robert Edgington, Austin, TX (US)

(73) Assignee: PARADROMICS, INC., Austin, TX (US)

( * ) Notice: Subject to any disclaimer, the term of this patent is extended or adjusted under 35 U.S.C. 154(b) by 0 days.

(21) Appl. No.: 16/275,205

(22) Filed: Feb. 13, 2019

(65) Prior Publication Data

US 2019/0246929 A1 Aug. 15, 2019

Related U.S. Application Data

(63) Continuation of application No. PCT/US2017/048759, filed on Aug. 25, 2017.
(Continued)

(51) Int. Cl.
*A61B 5/04* (2006.01)
*A61B 5/0476* (2006.01)
(Continued)

(52) U.S. Cl.
CPC .......... *A61B 5/04012* (2013.01); *A61B 5/04* (2013.01); *A61B 5/048* (2013.01); *A61B 5/0478* (2013.01);
(Continued)

(58) Field of Classification Search
None
See application file for complete search history.

(56) References Cited

U.S. PATENT DOCUMENTS

| 8,291,285 B1 | 10/2012 | Varnica et al. |
| 8,484,081 B2 | 7/2013 | Pradeep et al. |

(Continued)

FOREIGN PATENT DOCUMENTS

| JP | 4209781 B2 | 1/2009 |
| WO | WO-2011127483 A1 | 10/2011 |

(Continued)

OTHER PUBLICATIONS

Martins et al. A CMOS IC for Portable EEG Acquisition Systems. IEEE Transactions on Instrumentation and Measurement, vol. 47, No. 5, Oct. 1998. (Year: 1998).*
(Continued)

*Primary Examiner* — Etsub D Berhanu
(74) *Attorney, Agent, or Firm* — Wilson Sonsini Goodrich & Rosati

(57) ABSTRACT

Systems and methods for processing neural signals are provided. A neural data analysis system may comprise a feature extraction module configured to extract a plurality of features from neural signal waveforms obtained by an implanted neural interface probe with a plurality of channels or electrodes, and transmit the extracted features as a plurality of discrete outputs. The neural data analysis system may also comprise a feature-event coalescence module configured to receive the plurality of discrete outputs from the feature extraction module, and construct a model-based inference of bioelectric activity based on feature event statistics, prior knowledge of bioelectric signals, and/or a behavioral model of the feature extraction module. The neural data analysis system may further comprise an approximator module configured to receive a plurality of coalesced events from the feature-event coalescence module, and apply a series of transformations to the coalesced event data to generate a higher entropy neural code.

25 Claims, 12 Drawing Sheets

Related U.S. Application Data

(60) Provisional application No. 62/379,680, filed on Aug. 25, 2016.

(51) Int. Cl.
    *A61B 5/00*         (2006.01)
    *A61B 5/0478*    (2006.01)
    *A61B 5/048*     (2006.01)
    *A61N 1/05*      (2006.01)

(52) U.S. Cl.
CPC .......... *A61B 5/4064* (2013.01); *A61B 5/6868* (2013.01); *A61B 5/7239* (2013.01); *A61B 5/7246* (2013.01); *A61B 5/7253* (2013.01); *A61B 5/7242* (2013.01); *A61N 1/0531* (2013.01); *A61N 1/0534* (2013.01)

(56) References Cited

U.S. PATENT DOCUMENTS

| | | |
|---|---|---|
| 8,615,311 B2 | 12/2013 | Langhammer et al. |
| 8,892,208 B2 | 11/2014 | Flynn et al. |
| 9,449,225 B2 | 9/2016 | Ginosar et al. |
| 9,471,870 B2 | 10/2016 | Kao et al. |
| 2003/0158587 A1 | 8/2003 | Esteller et al. |
| 2004/0041599 A1 | 3/2004 | Murphy |
| 2005/0090756 A1 | 4/2005 | Wolf et al. |
| 2006/0116738 A1 | 6/2006 | Wolf et al. |
| 2006/0165811 A1 | 7/2006 | Black et al. |
| 2009/0082691 A1 | 3/2009 | Denison et al. |
| 2009/0118597 A1 | 5/2009 | Mills et al. |
| 2010/0081958 A1 | 4/2010 | She |
| 2013/0098780 A1 | 4/2013 | Georgiou et al. |
| 2013/0144140 A1 | 6/2013 | Frederick et al. |
| 2014/0018693 A1 | 1/2014 | Hou et al. |
| 2014/0025715 A1 | 1/2014 | Yang et al. |
| 2014/0051044 A1* | 2/2014 | Badower ................ A61B 5/165 434/236 |
| 2014/0163425 A1 | 6/2014 | Tran |
| 2014/0228701 A1 | 8/2014 | Chizeck et al. |
| 2014/0249396 A1 | 9/2014 | Shacham-Diamand et al. |
| 2015/0005607 A1 | 1/2015 | Cui et al. |
| 2015/0012111 A1 | 1/2015 | Contreras-Vidal et al. |
| 2016/0128588 A1 | 5/2016 | Melosh et al. |
| 2016/0199215 A1 | 7/2016 | Kopelman |
| 2016/0242690 A1 | 8/2016 | Principe et al. |
| 2016/0279418 A1 | 9/2016 | Courtine et al. |
| 2017/0042440 A1 | 2/2017 | Even-Chen et al. |

FOREIGN PATENT DOCUMENTS

| | | |
|---|---|---|
| WO | WO-2012116232 A1 | 8/2012 |
| WO | WO-2015164300 A1 | 10/2015 |
| WO | WO-2016112372 A1 | 7/2016 |
| WO | WO-2018039648 A1 | 3/2018 |

OTHER PUBLICATIONS

Csicsvari et al. Massively Parallel Recording of Unit and Local Field Potentials with Silicon-Based Electrodes. J Neurophysiol 90: 1314-1323, 2003. (Year: 2003).*

Kwon, et al., NeuroQuest: A comprehensive analysis tool for extracellular neural ensemble recordings, J Neurosci Methods. Feb. 15, 2012; 204(1): 189-201. doi:10.1016/j.jneumeth.2011.10.027.

PCT/US2017/048759 International Search Report and Written Opinion dated Nov. 8, 2017.

Akopyan, et al. A level-crossing flash asynchronous analog-to-digital converter. 12th IEEE International Symposium on Asynchronous Circuits and Systems (ASYNC'06). IEEE, 2006. 11pages.

Atreya, et al. Novel lossy compression algorithms with stacked autoencoders. Tech. Rep. (Dec. 11, 2009). 5 pages.

Barsakcioglu, et al. An analogue front-end model for developing neural spike sorting systems. IEEE Transactions on Biomedical Circuits and Systems 8.2 (Apr. 2014): 216-227.

Barsakcioglu, et al. Design optimisation of front-end neural interfaces for spike sorting systems. 2013 IEEE International Symposium on Circuits and Systems (ISCAS2013). IEEE, 2013. 2501-2504.

Chae, et al. A 128-channel 6 mW wireless neural recording IC with spike feature extraction and Uwb transmitter. IEEE Transactions on Neural Systems and Rehabilitation Engineering 17.4 (2009): 312-321.

Chen, et al. Asynchronous biphasic pulse signal coding and its CMOS realization. 2006 IEEE International Symposium on Circuits and Systems. IEEE, 2006. 2293-2296.

Chen, et al. Compressing neural networks with the hashing trick. International Conference on Machine Learning. 2015. 10 pages.

Co-pending U.S. Appl. No. 16/276,503, filed Feb. 14, 2019.

Dierikx, et al. Two-color indirect X-ray photon counting image sensor. Proc. 2013 Int. Image Sensor Workshop (IISW). 2013. 4 pages.

Goodfellow, et al. Measuring invariances in deep networks. Advances in Neural Information Processing Systems. 2009. 9 pages.

Harris, et al. Pulse-based signal compression for implanted neural recording systems. 2008 IEEE International Symposium on Circuits and Systems. IEEE, 2008. 344-347.

Kamboh, et al. Computationally efficient neural feature extraction for spike sorting in implantable high-density recording systems. IEEE Transactions on Neural Systems and Rehabilitation Engineering 21.1 (2013): 1-9.

Kamboh, et al. On-chip feature extraction for spike sorting in high density implantable neural recording systems. 2010 Biomedical Circuits and Systems Conference (BioCAS). IEEE, 2010.13-16.

Kozmin, et al. Level-crossing ADC performance evaluation toward ultrasound application. IEEE Transactions on Circuits and Systems I: Regular Papers 56.8 (2009): 1708-1719.

Lee, et al. Convolutional deep belief networks for scalable unsupervised learning of hierarchical representations. Proceedings of the 26th annual international conference on machine learning. ACM, 2009. 8 pages.

Morimoto, et al. Classifying the brain's motor activity via deep learning. Stanford University, CS 229 Machine Learning (2014). 5 pages.

Navajas, et al. Minimum requirements for accurate and efficient real-time on-chip spike sorting. Journal of Neuroscience Methods 230 (2014): 51-64.

Nurse, et al. A generalizable brain-computer interface (BCI) using machine learning for feature discovery. PloS One 10.6 (2015): e0131328. 22 pages.

Nurse, et al. Decoding EEG and LFP signals using deep learning: heading TrueNorth. Proceedings of the ACM International Conference on Computing Frontiers. ACM, 2016. 259-266.

Paraskevopoulou, et al. Feature extraction using first and second derivative extrema (FSDE) for real-time and hardware-efficient spike sorting. Journal of Neuroscience Methods 215.1 (2013): 29-37.

Paraskevopoulou, et al. Hierarchical Adaptive Means (HAM) clustering for hardware-efficient, unsupervised and real-time spike sorting. Journal of Neuroscience Methods 235 (2014): 145-156.

Ranzato, et al. Unsupervised learning of invariant feature hierarchies with applications to object recognition. Proc. Computer Vision and Pattern Recognition Conference (CVPR'07). IEEE Press. vol. 127. 2007. 9 pages.

Rastogi, et al. Integrate and fire circuit as an ADC replacement. 2011 IEEE International Symposium of Circuits and Systems (ISCAS). IEEE, 2011. 2421-2424.

Rogers, C. Ultra-Low power analog circuits for spike feature extraction and detection from extracellular neural recordings. Diss. University of Florida, 2007. 131 pages.

Rogers, et al. A pulse-based feature extractor for spike sorting neural signals. 2007 3rd International IEEE/EMBS Conference on Neural Engineering. IEEE, 2007. 490-493.

(56) References Cited

OTHER PUBLICATIONS

Saeed, et al. Hardware architecture for on-chip unsupervised online neural spike sorting. 2013 6th International IEEE/EMBS Conference on Neural Engineering (NER). IEEE, 2013. 1319-1322.
Schmidhuber, J. Deep learning in neural networks: An overview. Neural Networks 61 (Oct. 8, 2014): 85-117.
Stober, et al. Deep feature learning for EEG recordings. arXiv preprint arXiv:1511.04306 (2015). 24 pages.
Stober, et al. Using Convolutional Neural Networks to Recognize Rhythm Stimuli from Electroencephalography Recordings. Advances in Neural Information Processing Systems. 2014. 9 pages.
Todorova, et al. To sort or not to sort: the impact of spike-sorting on neural decoding performance. Journal of Neural Engineering 11.5 (Epub Aug. 1, 2014): 056005. 13 Pages.
Xu, J. Event-based compression circuits for neural recording. Diss. University of Florida, 2011. 153 pages.
Yen, et al. An integrated recording system using an asynchronous pulse representation. 2009 4th International IEEE/EMBS Conference on Neural Engineering. IEEE, 2009. 392-402.
Zheng, et al. An adaptive 16/64 kHz, 9-bit SAR ADC with peak-aligned sampling for neural spike recording. 2014 IEEE International Symposium on Circuits and Systems (ISCAS). IEEE, 2014. 2385-2388.
EP17844547.4 Extended European Search Report dated Mar. 12, 2020.
Rapoport et al. A Biomimetic Adaptive Algorithm and Low-Power Architecture for Implantable Neural Decoders. Proceedings of the 31st Annual International Conference of the IEEE Engineering in Medicine and Biology Society: Engineering the Future of Biomedicine, EMBC 2009, IEEE, pp. 4214-4217 (Sep. 3, 2009).

* cited by examiner

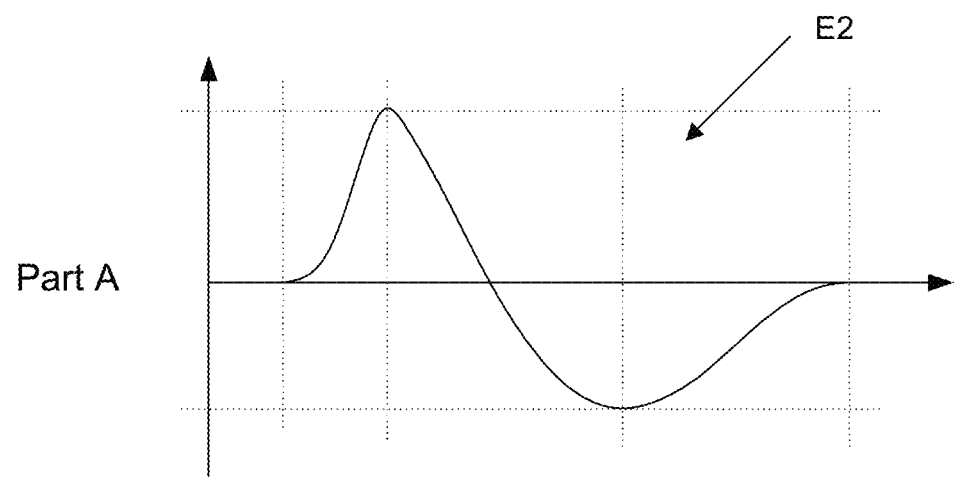
Part A
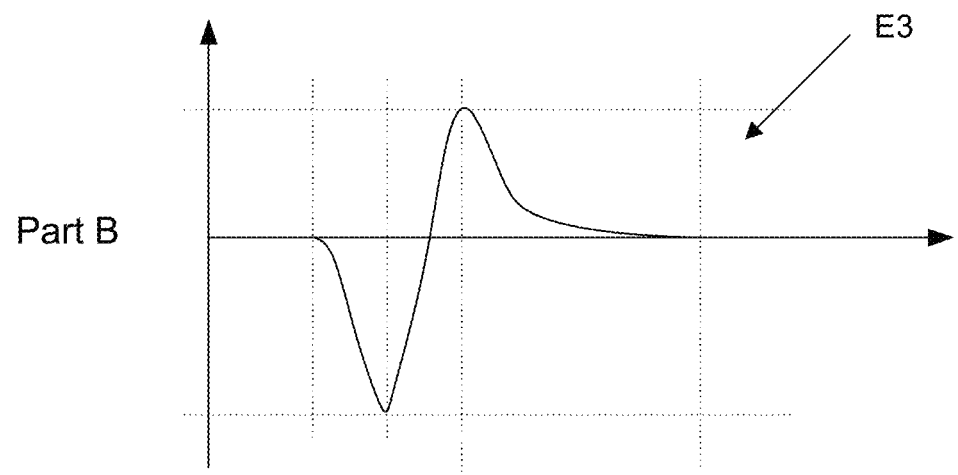
Part B
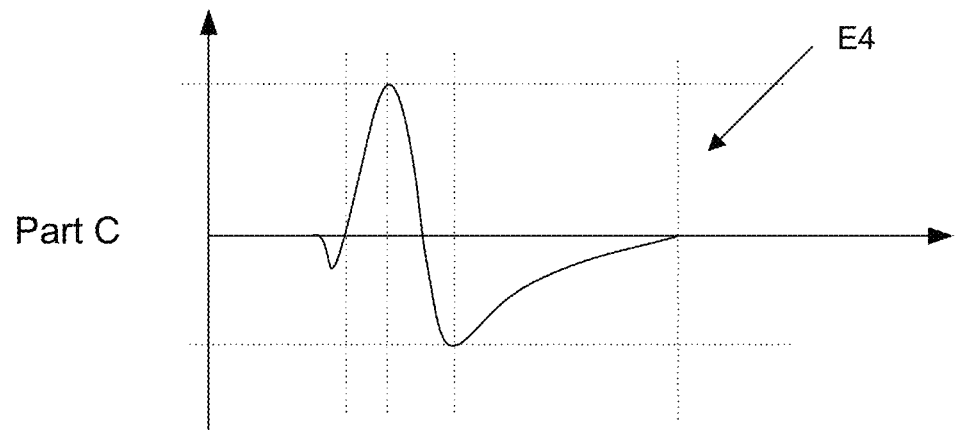
Part C
FIG. 3

SYSTEM AND METHODS FOR PROCESSING NEURAL SIGNALS

CROSS-REFERENCE

This application is a continuation application of international Application No. PCT/US2017/048759, filed on Aug. 25, 2017, which claims the priority of U.S. Provisional Patent Application No. 62/379,680, filed Aug. 25, 2016, which applications are incorporated herein by reference in their entirety.

STATEMENT AS TO FEDERALLY SPONSORED RESEARCH AND DEVELOPMENT

This invention was supported in part by a grant from the Defense Advanced Research Projects Agency (DARPA), contract no. N66001-17-C-4005. The Government has certain rights in the invention.

FIELD OF THE INVENTION

This invention relates to the use of a multi-module system for detecting the bioelectric activity of thousands, tens of thousands, hundreds of thousands, or millions of neurons and efficiently encoding the data stream associated with that activity in real-time. It utilizes a massively parallel array of electronic detectors to record important features of neural activity. It further coalesces these detected features into discrete bioelectric events or epochs based on a prior model of both the neural signal source and feature extraction circuitry. Finally, it finds alternative representations (or encodings) of this neural activity data that accomplish compression and/or dimensional reduction. These operations are all accomplished in a manner that reduces bandwidth and energy requirements, promotes miniaturization of the technology, and avoids dangerous heating of neural tissue.

BACKGROUND

The human brain is composed of nearly 100 billion neurons. Each neuron generates signals in the form of time-varying electrochemical potentials across their cellular membrane (action potentials). Due to its electrochemical nature, the timescale on which a single neural event takes place is orders of magnitude slower than electronic interactions implemented in a computer. Nonetheless, the human brain can leverage the interactions of many neurons to perform highly parallel computations. These complex signal cascades are responsible for all of the brain's information processing capabilities.

While neural circuits require the parallel action of many thousands, tens of thousands, hundreds of thousands, or millions of individual neurons, currently known methods for studying such circuits are typically only capable of measuring individual neural signals from a limited number of cells at a time. This limits understanding of how networks of many neurons give rise to the wide range of tasks performed by the brain. Thus, there is a need for systems and methods that are capable of detecting and processing neural events from a very large number of individual neurons. The results of the neural processing can provide a more in-depth understanding of how the brain functions. Such an understanding may allow treatment of disorders of the nervous system such as blindness, paralysis, and neurodegenerative diseases. Additionally, increasing the scale of interaction between man-made electronics and the human brain could lead to a new generation of high data rate brain-machine interfaces (BMIs) that can control complex prosthetics or mediate sensory input to the brain from devices such as digital cameras or microphones.

Processing information from a large number of individual neurons is a technological challenge due to the large amount of information generated. Continuous analog-to-digital conversion (ADC) of each neural action potential typically requires ADCs with high bit depths and sample rates. To process information from many thousands, tens of thousands, hundreds of thousands, or millions of neurons, bulky electronics and cables may be required, which may restrict body movement. In other instances, attempts to transmit fully sampled signals wirelessly from an implanted neural probe using current wireless technologies may cause undesirable heating of electronic circuits in the neural probe, and possibly result in damage to neural tissue.

Therefore, there is a need for systems and methods that are capable of detecting and processing neural events from a very large number of neurons, in a manner that minimizes the amount of information transmitted and heating emitted from an implanted neural probe while retaining enough information to generate useful data about the signals generated by many thousands, tens of thousands, hundreds of thousands, or millions of neurons.

SUMMARY OF THE INVENTION

The system and methods described herein can address at least the above needs. The system may be configured to receive a plurality of electrical signals from neural tissue. The electrical signals may be received from many thousands, tens of thousands, hundreds of thousands, or millions of individual neurons. The system may drastically reduce the bandwidth requirements for processing neural signals. The system may do so in a manner that avoids the loss of important information associated with known spike sorting techniques. Embodiments of the system may be particularly well suited for use in brain research applications, as well as in clinical applications, such as in the development of methods for treating nervous system disorders.

It is therefore an object of the present invention to disclose a neural recording and encoding system which comprises a feature extraction module and a feature-event coalescence module. The output from the feature extraction module forms the input to the feature-event coalescence module. The feature extraction module may detect neural action potential events from many thousands, tens of thousands, hundreds of thousands, or millions of neurons. In some embodiments, the events arise from extracellular measurements; in other embodiments, they arise from intracellular measurements. The events may arise from many thousands, tens of thousands, hundreds of thousands, or millions of electrodes. In some embodiments, the feature extraction module is embedded in neural tissue and the feature-event coalescence module is outside the body. In this case, information from the feature extraction module is transmitted wirelessly to the feature-event coalescence module. Alternatively, both the feature extraction module and the feature-event coalescence module are embedded in neural tissue. In this case, information from the feature-event coalescence module is transmitted outside of the body. In some embodiments, the transmission is via electromagnetic means capable of penetrating millimeters or centimeters of biological tissue. In some embodiments, the transmission is via millimeter wavelength transmission; in other embodiments, the transmission is via infrared (IR) optical means such as vertical cavity surface-emitting laser (VCSEL) arrays. The simple event detection module may be implemented in complementary metal oxide semiconductor (CMOS) technology. In some embodiments, the feature-event coalescence module is implemented using an application-specific integrated circuit (ASIC) or a field-programmable gate array (FPGA); in other embodiments, the feature-event coalescence module is implemented using a central processing unit (CPU) or general purpose graphics processing unit (GPGPU).

It is a further object of this invention to disclose a neural recording system which comprises a feature-event coalescence module and an approximator module. The approximator module may also be referred to as an approximator or approximation module. The output from the feature-event coalescence module forms the input to the approximator module. In some embodiments, the feature-event coalescence module is implanted in neural tissue and the approximator module is outside the body. In this case, information from the feature-event coalescence module is transmitted wirelessly to the approximator module. In other embodiments, both the feature-event coalescence module and the approximator module are located outside the body. The transmission may be via millimeter wavelength transmission; alternatively, the transmission may be via IR optical means such as VCSEL arrays; further alternatively, the transmission may be via ultra-wideband (UWB) transmission. The transmission may be a wired transmission, such as by a percutaneous lead. The percutaneous lead may carry neural signals from the electrodes to a location outside the body, such as a subject's chest. In some embodiments, the feature-event coalescence module is implemented in an ASIC or FPGA; in other embodiments, the feature-event coalescence module is implemented in a CPU or GPGPU. The approximator module may be performed using machine learning techniques. In some embodiments, the machine learning techniques are unsupervised machine learning techniques. In some embodiments, the machine learning techniques are semi-supervised machine learning techniques. In some embodiments, the machine learning techniques are supervised machine learning techniques. In some embodiments, the unsupervised machine learning techniques are autoencoder techniques. In some embodiments, the autoencoder techniques are multi-layer autoencoder techniques. In some embodiments, the approximator module is implemented in an ASIC or FPGA; in other embodiments, the approximator module is implemented in a CPU or GPGPU.

It is a further object of this invention to disclose a neural recording system which comprises a feature extraction module, a feature-event coalescence module, and an approximator module, wherein the output from the feature extraction module forms the input to the feature-event coalescence module and the output from the feature-event coalescence module forms the input to the approximator module.

In some embodiments, the feature extraction module detects neural action potential events from many thousands, tens of thousands, hundreds of thousands, or millions of neurons. In some embodiments, the events arise from extracellular measurements; in other embodiments, they arise from intracellular measurements. In some embodiments, the events arise from many thousands, tens of thousands, hundreds of thousands, or millions of electrodes. In some embodiments, the feature extraction module is embedded in neural tissue and the feature-event coalescence module is outside the body and information from the feature extraction module is transmitted wirelessly to the feature-event coalescence module. In other embodiments both the feature extraction module and the feature-event coalescence module are embedded in neural tissue and information from the feature-event coalescence module is transmitted outside of the body. The transmission may be via electromagnetic means capable of penetrating millimeters or centimeters of biological tissue. The transmission may be via millimeter wavelength transmission; alternatively, the transmission may be via IR optical means such as VCSEL arrays. In some embodiments, the simple event detection module is implemented in CMOS technology. In some embodiments, the feature-event coalescence module is implemented an ASIC or FPGA; in other embodiments, the feature-event coalescence module is implemented in a CPU or GPGPU.

In some embodiments, the feature-event coalescence module is implanted in neural tissue and the approximator module is outside the body and information from the feature-event coalescence module is transmitted wirelessly to the approximator module. In other embodiments, both the feature-event coalescence module and the approximator module are located outside the body. In some embodiments, the transmission is via electromagnetic means capable of penetrating millimeters or centimeters of biological tissue. In some embodiments, the transmission is via millimeter wavelength transmission; in other embodiments, the transmission is via VCSEL arrays; further alternatively, the transmission may be via ultra-wideband (UWB) transmission. The transmission may be a wired transmission, such as by a percutaneous lead. The percutaneous lead may carry neural signals from the electrodes to a location outside the body, such as a subject's chest. In some embodiments, the feature-event coalescence module is implemented in an ASIC or FPGA; in other embodiments, the feature-event coalescence module is implemented in a CPU or GPGPU. In some embodiments, the approximator module is performed using machine learning techniques. In some embodiments, the machine learning techniques are unsupervised machine learning techniques. In some embodiments, the machine learning techniques are semi-supervised machine learning techniques. In some embodiments, the machine learning techniques are supervised machine learning techniques. In some embodiments, the unsupervised machine learning techniques are autoencoder techniques. In some embodiments, the autoencoder techniques are multi-layer autoencoder techniques. In some embodiments, the approximator module is implemented in an ASIC or FPGA; in other embodiments, the approximator module is implemented in a CPU or GPGPU.

BRIEF DESCRIPTION OF THE DRAWINGS

The invention will now be described with reference to the drawings, wherein

FIG. 3 illustrates examples of other possible neural signal waveforms showing features to be extracted from the firing of other neurons, in accordance with some embodiments.

DETAILED DESCRIPTION OF THE INVENTION

Figure 1:
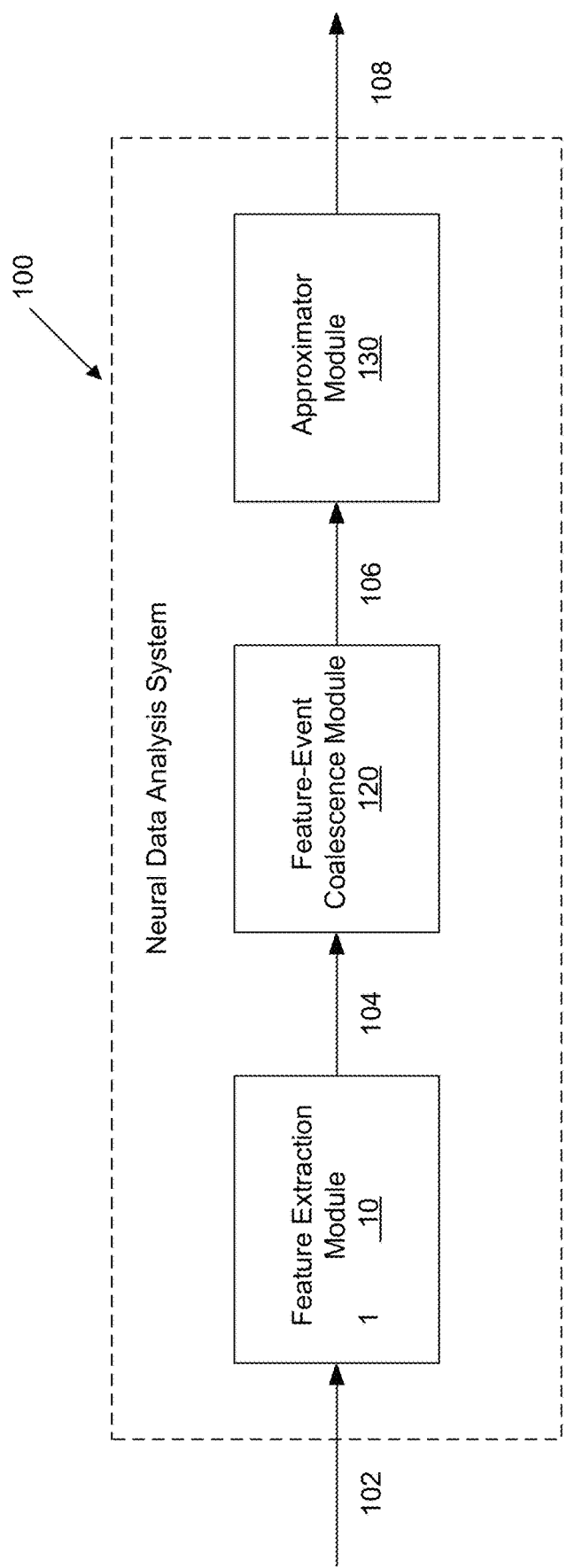
FIG. 1 illustrates a schematic block diagram of a neural data analysis system comprising a feature extraction module, a feature-event coalescence module, and an approximator module, in accordance with some embodiments.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The neural data analysis system described herein can act as a bridge between neural representations and digital representations. Since neural representations are indirectly observed by extracellular electrical recordings, the system can be configured to perform the following: (1) extract features from raw voltage waveforms that identify salient features of the waveforms pertaining to neural activity; (2) combine these features into discrete events based on a chosen prior, where events signify discrete patterns of bioelectric activity; and (3) use a machine learning method to learn an efficient decoding of latent information contained in the discrete events.

In operation (1), neural activity may be recorded from E electrodes to generate E recorded signals; E may be a positive integer and may have a value greater than 1,000, greater than 10,000, greater than 100,000, or greater than 1,000,000. E may have a value that is within a range defined by any two of the preceding values. In operation (2), a spike record for N putative neurons may be generated based on the E signals. N may be a positive integer and may generally have a value equal to or lesser than E. In operation (3), a machine learning method may determine a representation of the spike record that is significantly reduced in complexity. The machine learning method may be any machine learning method, including but not limited to one or more autoencoders, population vector decoders, Bayesian decoders, dynamical systems models, or neural networks (such as feedforward neural networks, recurrent neural networks, or long/short term memory networks).

In a preferred embodiment, the output of the feature extraction may be principal component (PC) scores that are sampled in an event-triggered manner. The event that triggers sampling of the PC scores may be a threshold crossing of the first PC score. In this case, feature-event coalescence may correspond to calculating a posteriori probability that a given neuron has fired based on the PC score.

An objective of the neural data analysis system and methods is to represent data coming from the brain in a form that is information-rich, denoised, and at low data rate. The invention can improve the viability of implantable brain-machine interfaces by minimizing heat dissipation in-situ and minimizing bandwidth requirements to transmit the signals out of the subject's brain, by means of a neural data processing pipeline that is tailored to denoising and reducing (or compression) of the data.

FIG. 1 illustrates a schematic block diagram of a neural data analysis system comprising a feature extraction module, a feature-event coalescence module, and an approximator module, in accordance with some embodiments. A neural data analysis system 100 may comprise a feature extraction module 110, a feature-event coalescence module 120, and an approximator module (also referred to as the approximator or approximation module) 130. The components within the neural data analysis system may be may be operatively connected to one another via a network or any type of communication links that allows transmission of data from one component to another. The neural data analysis system may be implemented using software, hardware, or a combination of software and hardware in one or more of the above-mentioned components within the system.

Neural information 102 may be collected using a neural interface probe (not shown) implanted into the brain. In some embodiments, the neural interface probe may comprise a plurality of wires, as described elsewhere herein. In some embodiments, the plurality of wires may comprise a flexible distal portion configured to interface with neural matter.

The neural information may include measured waveforms such as extracellular neuronal recordings and/or intracellular neuronal recordings. In some embodiments, an electrode array in a neural interface probe may comprise a plurality of microwires that are bonded to a readout integrated circuit (ROIC). In other embodiments, the electrodes may be patterned silicon probes or electrocorticography (ECoG) nets. In some instances, the ROIC and the electrodes may be fabricated from a same silicon substrate.

The feature extraction module is configured to receive and process the neural information and extract/output a set of discrete outputs 104 associated with the neural information. In doing so, the feature extraction module can decompose input high bandwidth signals from the neural information into groups of features (or discrete events) over time. For instance, instead of transmitting the raw voltage signal measured by an electrode, the feature extraction module may only transmit data when a putative action potential is detected. Instead of transmitting the full putative action potential waveform, it may only transmit a few descriptive bits of information associated with the putative action potential. In a simple embodiment, the feature extraction module may transmit one bit that indicates when a putative action potential is detected. The feature extraction module may transmit additional information. For instance, the feature extraction module may transmit several bits that encode different features of the putative action potential. In some embodiments, the feature extraction module transmits several bits that encode a correlation of the putative action potential waveform with a set of basis functions. In a preferred embodiment, the feature extraction module may perform a spectral decomposition such as principal components analysis (PCA), allowing communication of only a few bits of information per biological event (such as a putative action potential waveform).

The feature extraction may occur using analog hardware, such as a plurality of analog filters. The use of analog hardware may differ from other neural data pipeline systems that incorporate real-time digital processing of spiking neuron data. These systems may utilize a digitize-then-process paradigm which may not be scalable to handling information received from large numbers of electrodes. Such systems may be unsuitable for such applications due to the requirements of data rates that are so high that local digitization of the raw data cannot be attained within a reasonable power budget.

The feature extraction module may sample analog waveforms. The feature extraction module may be event driven. Though the feature extraction module may receive data from a large number of electrode channels, only channels that are currently active or were recently active may transmit data at any given point in time. Thus, the data rate may be significantly reduced when events are sparse, as is often the case with action potentials. Each channel may contain one or more sample and hold capacitors, which may impart analog memory and allow for event-driven readout of previous values of the channel. The analog values may be time-stamped and held in a memory buffer.

The feature-events output by the feature extraction module can be combined to construct a record of neural events. The rules for combining these feature-events are encoded in the feature-event coalescence module 120 and incorporate prior information/models about the physical origin of bio-electric signals as well as an explicit model of the feature extraction module and its input-output characteristics. The feature-event coalescence module 120 is configured to receive and process the discrete outputs from the feature extraction module, to generate a set of coalesced events 106.

The feature-event coalescence module may preserve waveform information insomuch as it provides additional information to the approximator module (such as by allowing signal source separation). However, the feature-event coalescence module may not impose a binary classification of spikes or perform so-called "spike sorting". The feature-event coalescence module may account for one or more known priors pertaining to either extracellular action potential waveforms or to the components of the feature extraction module. The feature-event coalescence module may serve as a hard-coded pre-processor of the output of the feature extraction module and may re-assemble a spike code. The feature-event coalescence module may combine event types arising across channels with high correlations. For instance, if a neuron is recorded on two channels simultaneously, or if the firing of a first neuron consistently (Probability ~1) triggers firing of a second neuron with a defined latency, only one event may be transmitted to the approximator module by the feature-event coalescence module. The feature-event coalescence module may undo unwanted effects obtained by the feature extraction module. For instance, the feature-event coalescence module may undo non-linearities in circuit elements such as amplifiers, defects arising due to the use of CMOS technologies, recording defects, or other unwanted effects. The unwanted effects may be removed by leveraging a priori knowledge of the effects, such as the known behavior of a circuit element.

The approximator module 130 is configured to receive and process the coalesced events to generate efficient encodings of neural states (neural code) 108. The neural code may then be transmitted to a traditional decoder that maps neural code onto external variables. The simplest form of a downstream decoder might be linear regression to an external variable such as the angle of a joint in for a prosthetic controller. The output of such a decoder is then used to operate external equipment (not shown). The external equipment may include devices such as speech synthesizers or prosthetics. Accordingly, real-time analysis of neural information using the system 100 may be used to control those devices, such as speech synthesizers or prosthetics.

The approximator module may find a compact description of neural code that is output by the feature-event coalescence module. The approximator may find patterns in spike timing and may seek to compress data on the basis that neuronal firing rates are highly correlated (and thus data from spiking neuron populations is low entropy). The approximator module may serve to infer a graphical network topology from the spike record. The approximator module may perform lossless or lossy compression of the graphical network. The compression may discard a portion of redundant highly correlated spike sources. Unlike traditional decoders, the approximator module may require no prior knowledge about neural firing and no external variables with which to correlate neural activity.

Although described above as comprising a feature extraction module, a feature-event coalescence module, and an approximator module, the neural data analysis system 100 may lack a feature-event coalescence module in some cases. In some instances, output from the feature extraction module may be passed directly to the approximator module. In some instances, elements of the feature-event coalescence module may be incorporated into the approximator module.

The extraction of discrete events in the feature extraction module may act to encode neural information in a form of lower dimensionality. Extracellular voltage recording produces signals that are sparse. Detected extracellular action potential waveforms originate from neuronal action potential events that have a duration of only a few ms and occurring at an average rate of approximately 5 Hz. Additionally, action potentials contain high frequency information (>10 kHz), but they are very stereotyped in temporal dynamics. Both the sparsity of action potentials and their stereotypical behavior may make neural signals very compressible. The feature extraction module may be viewed as enacting a form of compressed sensing on the neural information, extracting the timing and a small set of features from each action potential, thereby reducing the amount of digital information required to describe neural signals. In some embodiments, the feature extraction module may perform compression by a factor of about 10 to about 1,000. The feature extraction module may perform compression by a factor that is within a range defined by the two preceding values.

The feature-event coalescence module is also configured to reduce the total amount of data required to represent the essential features of neural activity, and to organize it in accordance with a strong prior about neural signals. It acts by coalescing (grouping) the discrete events into a smaller number of coalesced events with greater information per event. Additionally, it applies prior knowledge of the detection circuitry to remove artifacts and redundant events. Concretely, this means determining which events were part of a bona fide action potential voltage waveform, which were part of the same action potential waveform, and what were the important features of each waveform (e.g. rise-time, action potential half-width). The feature-event coalescence may also infer which action potential waveforms originate from the same neuron or from two or more neurons with highly correlated firing rates. The feature-event coalescence may ascribe a posterior probability of class membership to each detected event. The feature-event coalescence may ascribe the posterior probability based on Bayesian methods, Gaussian mixture models, fuzzy k-means, logistical regression, or any other statistical inference method. The posterior probabilities may be subjected to thresholding, such that a putative action potential event is definitively assigned to a particular neuron if the posterior probability meets or exceeds a threshold. In some cases, such discretization may not be desired and the posterior probabilities themselves may be output by the feature-event coalescence.

Feature-event coalescence may differ from "spike sorting" in two critical ways. Firstly, the feature-event coalescence module may be configured to generate coalesced events without needing to classify each event as relating to a particular neuron but without discarding the features that would otherwise make such classification possible. Discarding of recorded action potentials that cannot be classified as relating to a particular neuron is characteristic of spike sorting methods. Secondly, the feature-event coalescence step is optimized to preserve information contained in the population activity rather than optimized for inferring the identity/location of the neurons engaged in brain computation. Indeed, spike sorting often leads to equal or worse decoding performance versus approaches that make no effort at source localization, because it explicitly throws out data in the analysis. Our approach by contrast seeks to use all of the putative action potential data that is collected. In some embodiments, the feature-event coalescence module may perform further compression by a factor of up to 10.

Finally, another way in which feature-event coalescence can reduce bandwidth is that it may include temporal downsampling. Though the simple events may be detected with high temporal precision (e.g. 10-20 kHz) in order to encode high frequency component features of the action potential waveform, once coalesced, the events themselves only need approximately 1 ms timing.

Thus, the feature extraction module and the feature-event coalescence module can collectively compress the amount of information to be processed by the approximator module. In some embodiments, the feature extraction module and the feature-event coalescence module may collectively compress the information to be processed by the approximator module, by a factor of 100 to 10,000. This high level of compression can significantly reduce the computational load on the approximator module.

The approximator module 130 is configured to process the coalesced events 106 to extract a meaningful representation of the neural information. For example, the approximator module can generate a set of neural code 108 from the coalesced events. The neural code may correspond to a highly compressed meaningful representation of a stream of neural information. In some embodiments, this neural code may be further sent to a decoder or other external devices and/or used by those devices to control one or more activities of a human subject. The neural code may instruct a device to execute one or more physical or non-physical activities, such as moving a robotic arm in response to detecting a subject's intention to move his or her arm, navigating the Internet, making a phone call, turning on lights or other Internet-connected devices, or executing any other physical or non-physical activity.

In some embodiments, the system of FIG. 1 can be represented as three stages of a neural data processing pipeline: (1) feature extraction; (2) feature-event coalescence; and (3) approximator.

In the first stage, voltage-over-time signal coming from a neural interface probe may be analyzed by a number of condition circuits. The condition circuits may include passive or active filter circuits that summarize some aspect of the signal into one or a few digital bits or a few digital values (such as 8-bit or larger numbers), and that are described as discrete events $s_i$, where i is an integer.

The second stage may coalesce discrete events, subject to the conditions as described elsewhere herein.

The third stage, the approximator, performs a method for denoising and reducing the neural event data according to a set of biases and priors, some of which may be imposed by the method itself, and some of which may be imposed in addition to the method (regularization).

The following figures and description describe in detail how various components of the neural data analysis system function to process neural information.

Figure 2:
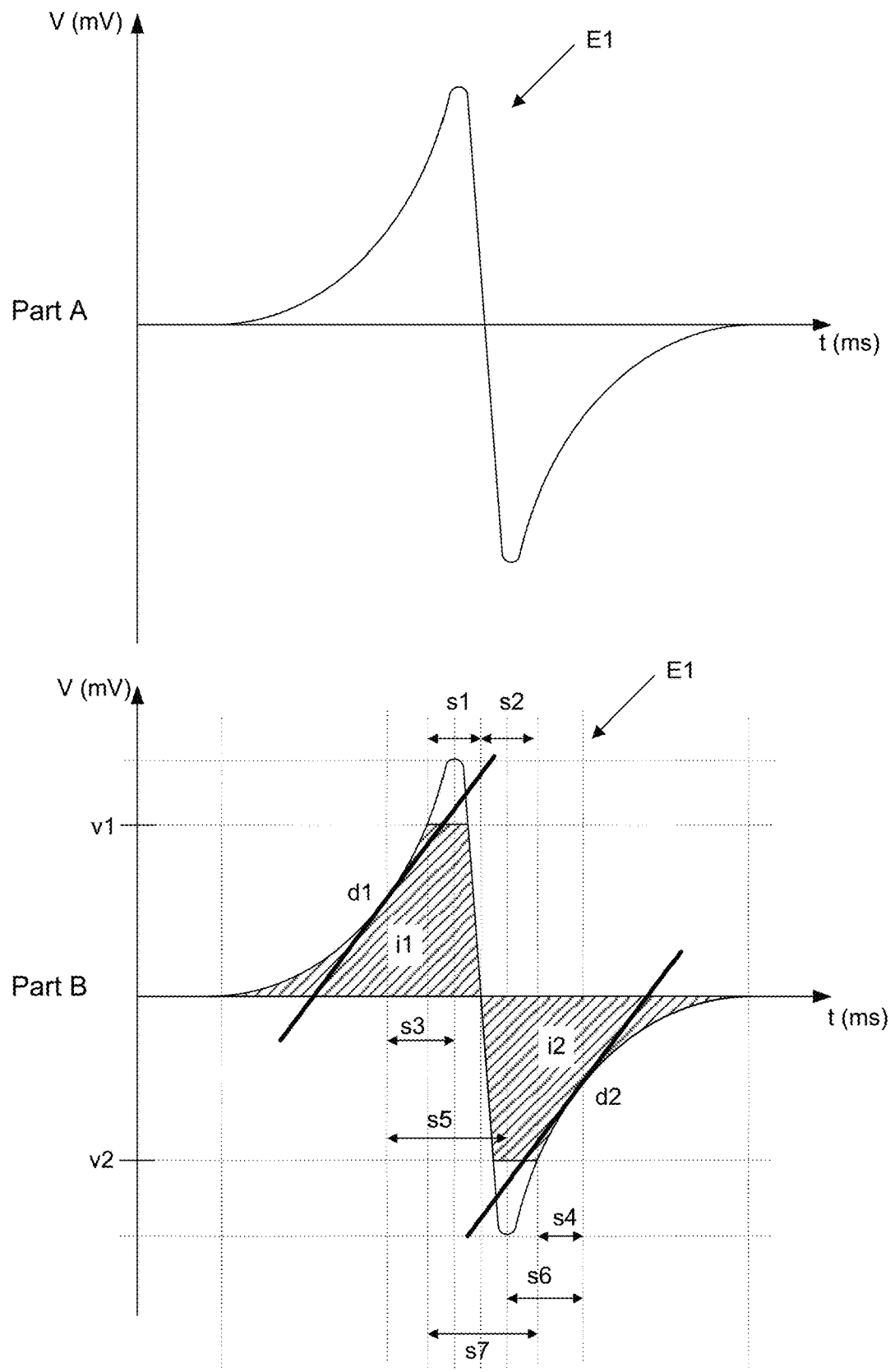
FIG. 2 illustrates an idealized neural signal waveform showing features to be extracted from the firing of a single neuron, in accordance with some embodiments.

FIG. 2 illustrates an idealized neural signal waveform showing features to be extracted from the firing of a single neuron, in accordance with some embodiments. Part A of FIG. 2 illustrates an electrical signal E1 from the firing of a neuron. The electrical signal results from the buildup of unbalanced electrical charge on either side of the neuron cell membrane as ions are transported in and out of the cell. This results in a time-varying membrane potential and serves as the neuron's means of computation. Five basic phases can be generally defined in the course of the firing of a single neuron. Initially, the neuron is in a state of rest where it is negative relative to the extracellular solution. Over time, the membrane potential rises and the neuron becomes positively charged relative to the extracellular solution. When the membrane potential reaches a critical saturated value (e.g., approximately 80 mV), the membrane potential is quickly driven negative, to an inversion state (hyperpolarization). The neuron then enters a state of recovery (refractory period) until it has returned to its resting state. This describes the basic profile of an intracellular action potential, which can propagate through the tree-like morphology of a neuron. The propagation of this wave of electrochemical potential along the neural membrane results a complex flow of ionic currents around the neuron, which results in time-varying potential in the area around the neuron. This is the extracellular action potential waveform, which can be heterogeneous depending on neuron geometry and type but is usually an order of magnitude smaller in amplitude relative to the intracellular potential. In the preferred embodiment, this is the signal that is recorded.

Action potential waveforms contain power at high frequencies (>10 kHz), and this high frequency component can provide useful information for decoding, allowing the decoder to discriminate between two waveforms recorded on the same electrode. In order to satisfy the Nyquist sampling criterion, the waveform may have to be sampled at a frequency of e.g. 20 kHz or higher. In addition, the wide dynamic range in membrane potential could require the use of analog-to-digital converters (ADCs) with high bit depths. For example, 12-bit or 16-bit ADCs are often used to accurately record neural signals for research purposes. A sampling rate of 20 kHz with a bit depth of 16 corresponds to a data rate of up to 320 kb/s for a single neuron. The sampling of many thousands, tens of thousands, hundreds of thousands, or millions of neurons at a time requires transmission and processing of a large amount of data (e.g. many gigabits of data per second). Such high data rates typically require the use of high bandwidth transmission cables, which may restrict a human subject's mobility. Moreover, the high data rate may cause undesirable heating of electronic circuits in the implanted neural interface probe, which may result in damage to neural tissue.

The neural data analysis system disclosed herein can obviate the above drawbacks relating to high bandwidth transmission and potential overheating of neural tissue. Unlike conventional Nyquist sampling methods, the exemplary neural data analysis system can be used to substantially compress the information needed to describe neural processes. In some embodiments, the feature extraction module may be configured to only output data (discrete events) upon determining that the neural information satisfies one or more conditions.

Part B of FIG. 2 illustrates features that can be extracted from the firing of a single neuron, in accordance with some embodiments. The feature extraction can be performed with a reduced number of bits, and without requiring sampling of the neural signal waveform at the Nyquist rate. In some embodiments, the electrical signal E1 can be represented by a set of discrete events: {s1, s2, s3, s4, s5, s6, s7}. Any number of discrete events may be defined and/or contemplated. Without limitation and by way of example, such discrete events may include comparing an aspect of a neural signal (such as a membrane potential) with a previously-defined condition or attribute, and noting the time points at which the neural signal falls within a predetermined threshold to the previously-defined condition or attribute. Other discrete events may include comparing aspects of a transformed neural signal.

The set of discrete events may be represented by different time signals that are recorded and associated with different neural signals. For example, in some embodiments, s1 may correspond to a time period during which the neural signal exceeds a positive threshold value v1. s2 may correspond to a time period during which the neural signal falls below a negative threshold value. s3 may correspond to a time period during which the first time derivative of the neural signal exceeds a positive first time derivative threshold value d1. s4 may correspond to a time period during which the first time derivative of the neural signal falls below a negative first time derivative threshold value d2. In some cases, second and higher order time derivatives may be used in the extraction of discrete events. Similarly, time integrals can be used in the extraction of discrete events. s5 may correspond to a time period during which the time integral of the neural signal exceeds a positive time integral threshold value i1. s6 may correspond to a time period during which the time integral of the neural signal falls below a negative time integral threshold value i2. In some cases, the time integral may be a leaky integral, which can reduce the recording of spurious discrete events associated with noise in the baseline of the neural waveform.

In some cases, comparisons between the times at which different discrete events are recorded may themselves constitute discrete events. For instance, s7 may correspond to a time period between the neural signal rising above a positive threshold value v1 and falling below a negative threshold value v2. A discrete event as described herein may comprise any information to be extracted from a neural signal waveform, and which may aid in further processing downstream.

FIG. 3 illustrates examples of other neural signal waveforms showing features to be extracted from the firing of other neurons, in accordance with some embodiments. Specifically, Parts A, B, and C of FIG. 3 illustrate the waveforms of different electrical signals E2, E3, and E4, respectively. The electrical signal E2 may differ from the electrical signal E1 by longer or shorter states of dormancy, polarization, inversion, or recovery. The electrical signal E2 may also differ from E1 by different values of the positive and negative saturation neural signal. In some embodiments, the electrical signal E2 may be represented by a different set of discrete events {s1', s2', s3', s4', s5', s6', s7'}. s1' may represent the time period during which the neural signal has a value exceeding a positive threshold value v1'. s2' may represent the time period during which the neural signal has a value falling below a negative threshold value v2'. s3' may represent the time period during which the neural signal has a first time derivative exceeding a positive first time derivative threshold value d1'. s4' may represent the time period during which the neural signal has a first time derivative falling below a negative first time derivative threshold value d2'. s5' may represent the time period during which the neural signal has a time integral exceeding a positive time integral threshold value i1'. s6' may represent the time period during which the neural signal has a time integral falling below a negative time integral threshold value i2'. Second and higher order time derivatives may also be of interest for the recording of discrete events. For example, s7' may represent the time period between the neural signal rising above a positive threshold value v1' and falling below a negative threshold value v2'. Additional events may represent one or more times at which a neural signal has a peak maximum or trough minimum value.

Parts B and C of FIG. 3 illustrate other signal waveforms E3 and E4 associated with other possible neuronal firings. The electrical signal E3 may be associated with any combination of discrete events s1", s2", s3", s4", s5", s6", and s7", etc. associated with neural signal values, first time derivatives, time integrals, and timings between events, as well as additional events associated with second or higher order time derivatives and/or other discrete events. Likewise, the electrical signal E4 may also be associated with any combination of discrete events s1''', s2''', s3''', s4''', s5''', s6''', and s7''', etc. associated with neural signal values, first time derivatives, time integrals, and timings between events, as well as additional events associated with second or higher order time derivatives and/or other discrete events.

In some embodiments, the condition circuit may be subjected to a transformation to transform the neural signal into one or more continuous transformed output signals. Discrete events may then be extracted from these transformed output signals instead of or in addition to the neural signal itself. The transformations may comprise one or more analog or digital transformations of the signal. The transformations may be linear or nonlinear transformations. The transformations may be a correlation or convolution of the neural signal with one or more filters, which may make up a basis set of transforms. Such basis sets may comprise transforming the neural signal into one or more transformed outputs. The transformation operations may be composed from prior knowledge taken from a library of neural signals. For example, the transform operations may perform a spectral decomposition of the signal wherein the transfer functions of the transformation operations may have impulse responses which resemble eigenvectors derived from spectral analysis of some part or whole of a historic neural signal. Such spectral decomposition methods may comprise principal component analysis (PCA), factor analysis, linear discriminant analysis (LDA), independent component analysis (ICA), kernel PCA (kPCA), optimized kernel entropy components, or any other statistical inference method. In a preferred embodiment, a neural signal is transformed in a correlation operation with the first 3 principal components (PCs) to give 3 transformed outputs corresponding to continuous time-varying PC scores.

In some embodiments, a basis set may be used with no prior knowledge of the signal. For instance, the basis set may comprise a wavelet basis set, or an arbitrary finite impulse response filter (FIR). The FIR filters may include integration and differentiation operations.

Figure 4:
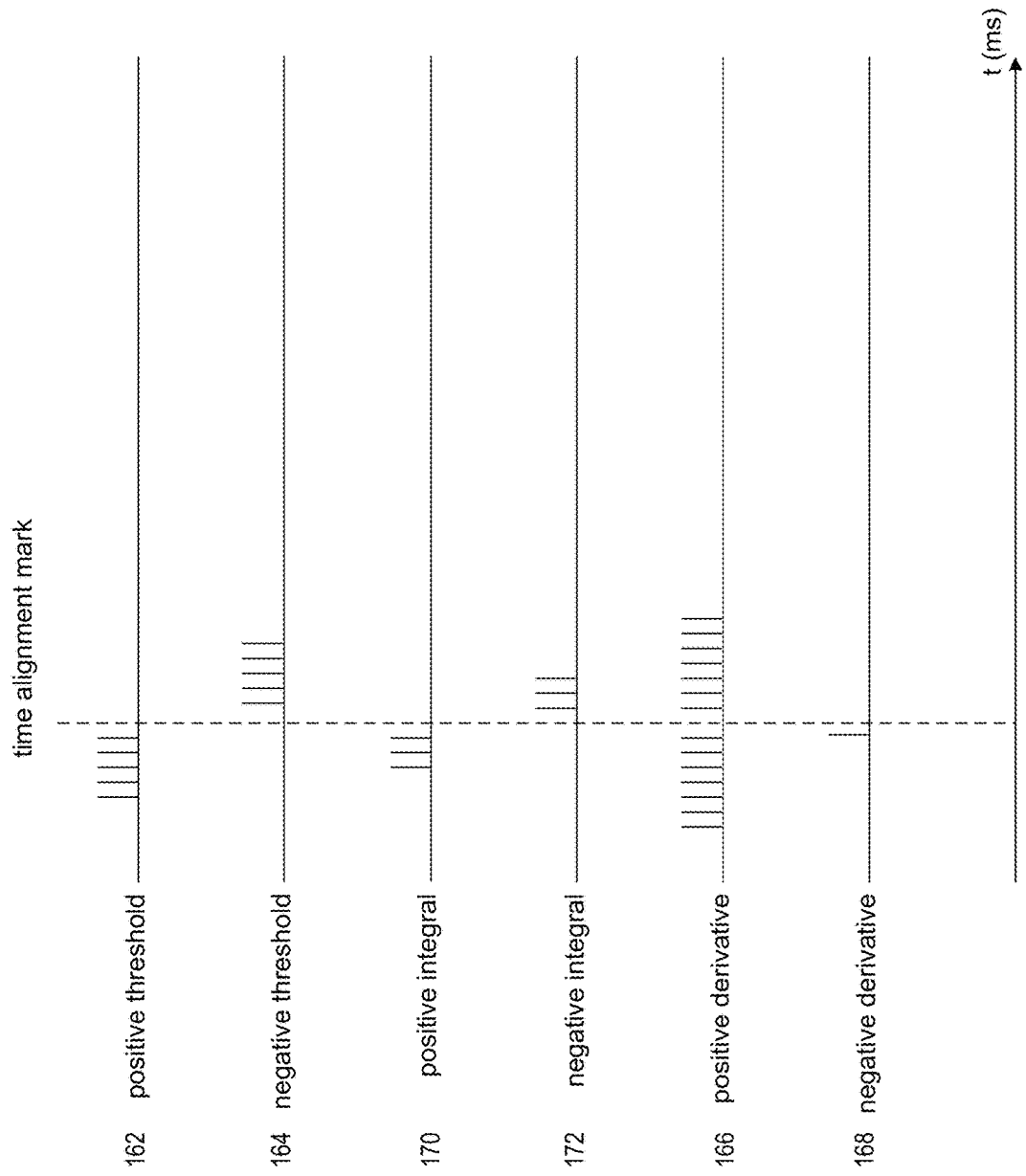
FIG. 4 illustrates an exemplary output from an array of discrete event detectors, in accordance with some embodiments.

FIG. 4 illustrates an exemplary output from an array of discrete event detectors, in accordance with some embodiments. The output may be associated with the firing of a single neuron. The array of discrete event detectors may be implemented in, or as part of the feature extraction module.

In some embodiments, the array of discrete event detectors may comprise a positive threshold channel 162, a negative threshold channel 164, a positive first time derivative threshold channel 166, a negative first time derivative threshold channel 168, a positive time integral threshold channel 170, and a negative time integral threshold channel 172. The abovementioned channels can be used to detect the various discrete events shown in FIG. 2B. For example, the positive threshold channel 162 can be used to detect discrete event s1, which corresponds to a time period during which the neural signal exceeds a positive threshold value v1. The negative threshold channel 164 can be used to detect discrete event s2, which corresponds to a time period during which the neural signal falls below a negative threshold value. The positive first time derivative threshold channel 166 can be used to detect a discrete event s3, which corresponds to a time period during which the first time derivative of the neural signal exceeds a positive first time derivative threshold value d1. The negative first time derivative threshold channel 166 can be used to detect discrete event s4, which corresponds to a time period during which the first time derivative of the neural signal falls below a negative first time derivative threshold value d2. One or more additional channels can be used to obtain information about second and higher order time derivatives. For example, the positive integral threshold channel 168 can be used to detect discrete event s5, which corresponds to a time period during which the time integral of the neural signal exceeds a positive time integral threshold value i1. The negative integral threshold channel 170 can be used to detect discrete event s6, which corresponds to a time period during which the time integral of the neural signal falls below a negative time integral threshold value i2.

One or more additional channels can be used to obtain coded representations of comparisons between the times at which different discrete events are recorded. For instance, discrete event s7 may correspond to a time period between the neural signal rising above a positive threshold value v1 and falling below a negative threshold value v2. As previously described, a discrete event may comprise any information extracted from the neural signal waveform which may aid in further processing downstream.

In some embodiments, a logical combination of one or more events detected by one or more electrodes may be used as a trigger to sample events or values on one or more other electrodes. The values sampled from the trigger may require no defining characteristic to classify them as an event per se. For instance, the values sampled from the trigger may be an analog value of an electrode at one instance. For example, a threshold crossing on a first electrode may be used to immediately sample a value on second and third electrodes. In this example and in a preferred embodiment, the first electrode value may correspond to a first PC (PC1) score, and the second and third electrode values may correspond to second and third PC (PC2 & PC3) scores, respectively. In some embodiments, an event recorded by one channel may disable the acquisition of events on one or more other channels.

An example of a coded representation via a channel is described as follows. Each channel may output a bit state of 1 only at times during which a predefined condition holds true. Accordingly, each channel may produce information that encodes features of the neural waveform E1 only during those times at which the predefined condition is met. For instance, the positive threshold channel 162 may generate a series of bits with a value of 1 only for the time period s1 during which the neural signal exceeds a positive threshold value v1. The negative threshold channel 164 may generate a series of bits with a value of 1 only for the time period s2 during which the neural signal falls below a negative threshold value. The positive first time derivative threshold channel 166 may generate a series of bits with a value of 1 only for the time period s3 during which the first time derivative of the neural signal exceeds a positive first time derivative threshold value d1. The negative first time derivative threshold channel 166 may generate a series of bits with a value of 1 only for the time period s4 during which the first time derivative of the neural signal falls below a negative first time derivative threshold value d2. One or more additional channels may code information about second and higher order time derivatives. For example, the positive integral threshold channel 168 may generate a series of bits with a value of 1 only for the time period s5 during which the time integral of the neural signal exceeds a positive time integral threshold value i1. The negative integral threshold channel 170 may generate a series of bits with a value of 1 only for the time period s6 during which the time integral of the neural signal falls below a negative time integral threshold value i2.

Since discrete events may occur sparsely in time compared to the entire duration of a waveform E1, the use of an array of discrete event detectors can significantly reduce the data sampling rate required, in contrast to Nyquist condition sampling rates for complete reconstruction of a waveform, as previously described. Instead of acquiring samples of the neural waveform at a uniform rate, the various channels of the feature extraction module may generate data only during the times at which certain predefined conditions or criteria are met (see e.g., part B of FIG. 2, and FIG. 4). This method of sparse but relevant sampling may significantly decrease the required average sampling rate. Moreover, the relatively binary nature of some embodiments of the discrete events requires the use of only one or a few bits to record each discrete event. When compared to the multiple samples of 12-16 bit depth required for full reconstruction of a waveform, the exemplary method of encoding disclosed herein can provide further reduction of the data transmission rate for monitoring the signals from a single neuron. The lower average sampling rate and decreased bit depth can collectively reduce the required data transmission rate by a factor of 10-1000, depending on the exact embodiment in hardware.

Figure 5:
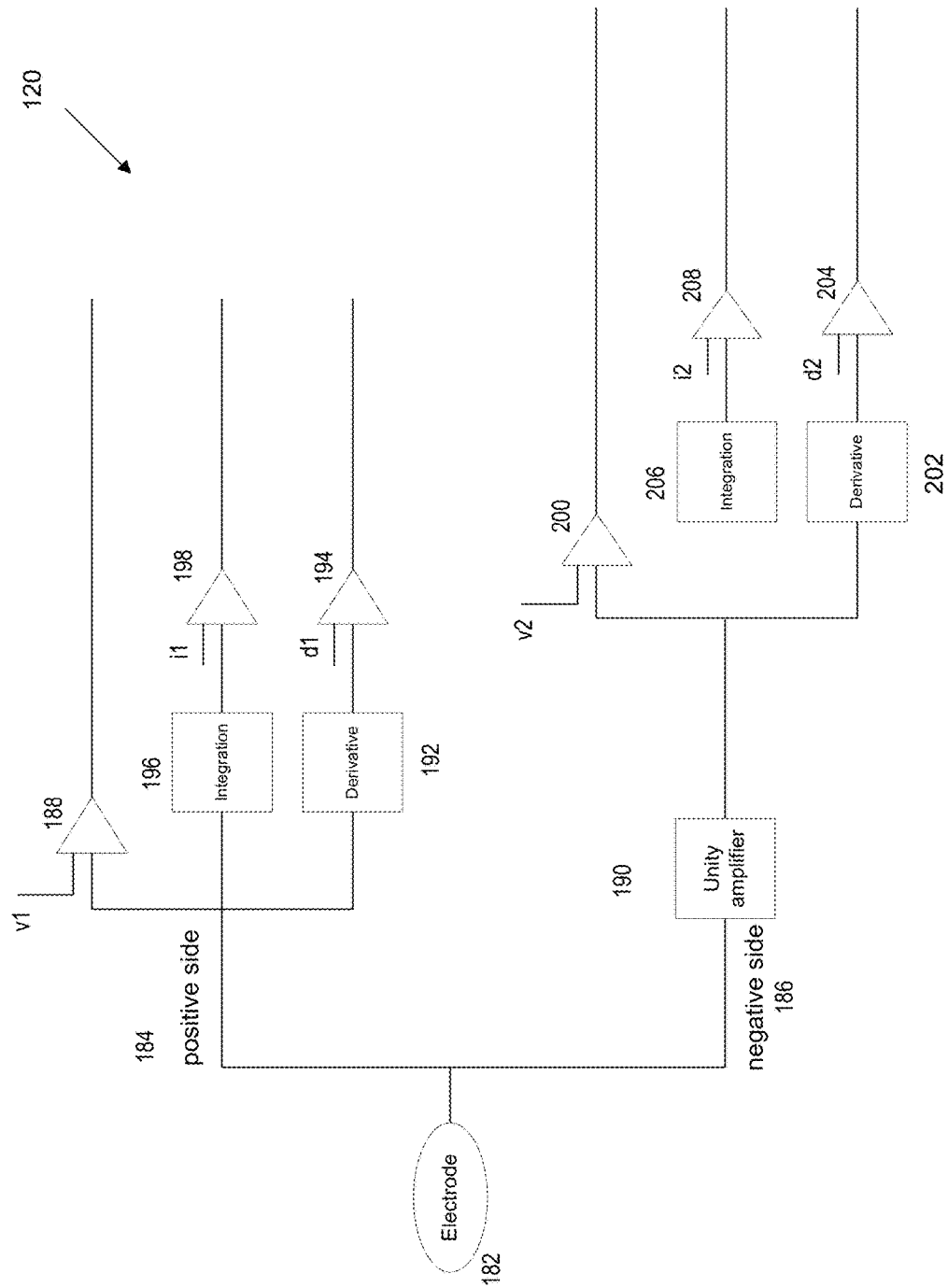
FIG. 5 illustrates a discrete event detector comprising an electronics detection cascade for detecting one or more discrete events associated with the firing of a single neuron, in accordance with some embodiments.

FIG. 5 illustrates a discrete event detector comprising an electronics detection cascade for detecting one or more discrete events associated with the firing of a single neuron, in accordance with some embodiments. Neural signals may be obtained using an electrode 182 implanted in neural tissue. The electrode may be part of a neural interface probe. The neural signals detected by the electrode may be indicative of extracellular membrane potentials or intracellular membrane potentials. The neural signals may be amplified by one or more electronic amplifiers or pre-amplifiers (not shown). The amplified neural signal may be routed in parallel into one or more transformation operators. The operators may perform correlation operations to output, for instance, the PC1, PC2, and PC3 scores of the neural signal based on PC data generated from PCA analysis from an ergodic (or otherwise sufficiently representative) library of neural spike waveforms. A detector may then inspect the PC1 output for a magnitude threshold crossing event (s1) and local maxima or minima event (s2), to make an AND logic combined event s3. The s3 event may then trigger a sparse value sampling of PC1, PC2 & PC3 to give 3 event samples (each of which may be 8 bits in length or longer). The operators may perform correlation operations to output any number of PC scores.

The amplified signals may be passed to the circuit of FIG. 5. The circuit of FIG. 5 may be wired in parallel to implement a positive bank of detectors 184 and a negative bank of detectors 186. A number of comparison elements may be provided in parallel in the positive bank. A positive threshold comparator 188 may compare the neural signal with a reference voltage and produce a signal only during the times s1 (during which the neural signal exceeds a positive threshold value v1). The positive bank may also include a differentiation element 192 configured to perform a first time derivative on the neural signal. A positive first time derivative threshold comparator 194 may compare the positive first time derivative with a reference voltage and produce a signal only during the times s3 (during which the positive first time derivative exceeds a positive first time derivative threshold value d1). The positive bank may also include an integration element 196 configured to perform a time integral on the neural signal. A positive time integral threshold comparator 198 may compare the positive first time derivative with a reference voltage and produce a signal only during the times s5 (during which the positive first time derivative exceeds a positive first time derivative threshold value i1).

The electrical signal at the negative side 186 may be inverted using a unity gain inverting amplifier 190. A number of comparison elements may be provided in parallel in the negative bank. A negative threshold comparator 200 may compare the neural signal with a reference voltage and produce a signal only during the times s2 (during which the neural signal falls below a negative threshold value v2). The negative bank may also include a differentiation element 202 configured to perform a first time derivative on the neural signal. A negative first time derivative threshold comparator 204 may compare the negative first time derivative with a reference voltage and produce a signal only during the times s5 (during which the negative first time derivative falls below a negative first time derivative threshold value d2). The negative bank may also feature an integration element 206 configured to perform a time integral on the neural signal. A negative time integral threshold comparator 208 may compare the negative first time derivative with a reference voltage and produce a signal only during the times s6 (during which the positive first time derivative falls below a negative first time derivative threshold value i2).

One or more additional circuit elements may be implemented to perform comparisons between the times at which different discrete events are recorded. For instance, the time s7 between the neural signal rising above a positive threshold value v1 and falling below a negative threshold value v2 may be detected utilizing appropriate circuit elements.

In some embodiments, the circuit of FIG. 5 (or a discrete event detector) may be implemented in the CMOS electronic circuitry of an active pixel sensor in a ROIC of a neural interface probe. The discrete event detector may be configured to perform feature extraction (or compressed sensing). Each active pixel may include one or more condition circuits comprising an analog circuit and low-resolution analog-to-digital converter(s). These condition circuits are designed to detect specific temporal features in the voltage signal ("conditions" or events). These conditions/events may include, for example: (1) the signal reaching a certain value (first threshold), (2) the derivative of the signal reaching a certain value (second threshold), or (3) a leaky integrator reaching a certain value (third threshold). A condition may also include a ratiometric criterion such as comparing the relative power in two frequency bands or some other normalized measurement. The condition(s) may be assessed at a sampling rate (for example, 1 kHz) considerably lower than the Nyquist sampling rate needed to fully capture the input signal.

The active pixel sensor may be defined by a width×height number of pixels, each of which contains a bank of condition circuits in our invention. An example of a condition circuit is a threshold filter.

The in-pixel detection circuitry can convert the measured analog voltage-over-time signal into a series of digital events (discrete events), each of which is comprised of one or more bits summarizing salient aspects of the signal. The circuitry can be designed to detect features of the action potential waveform so that the event record captures all information about the neural activity.

A series of discrete events can be transmitted using relatively low voltage and power (compared to analog), thus reducing the total amount of power dissipated in the implant and decreasing the health risk to the recipient of the implanted neural interface probe.

Using the system described herein, the action potentials can be resolved to within 1 ms timing resolution. Since each electrode can measure neural signals from a plurality of different neurons (such as 8 different neurons), a minimum sampling rate of 4 bits*1,000 samples per second=4 kb/s can distinguish between the different neuron sources. Allowing for some buffer (e.g. of up to 4 additional bits), this may translate to 4-8 Gb/s for 1 million electrodes, which is a data rate that is supported by commercial wireless technology, such as 60 GHz transceiver technology. In another exemplary calculation of the data transmission requirements, one or more score values (such as 2-3 score values) per spike may be reported when sampling event values from transformed input signals. For an average firing rate of 5 Hz, an average of 8 neurons per electrode, and a bit depth of 10 bits, 8*10 bits*5 samples per second=0.4 kb/s can distinguish between neuron sources. This may translate to 0.4 Gb/s for 1 million electrodes, which is once again a data rate that is supported by commercial wireless technology, such as 60 GHz transceiver technology.

Figure 6:
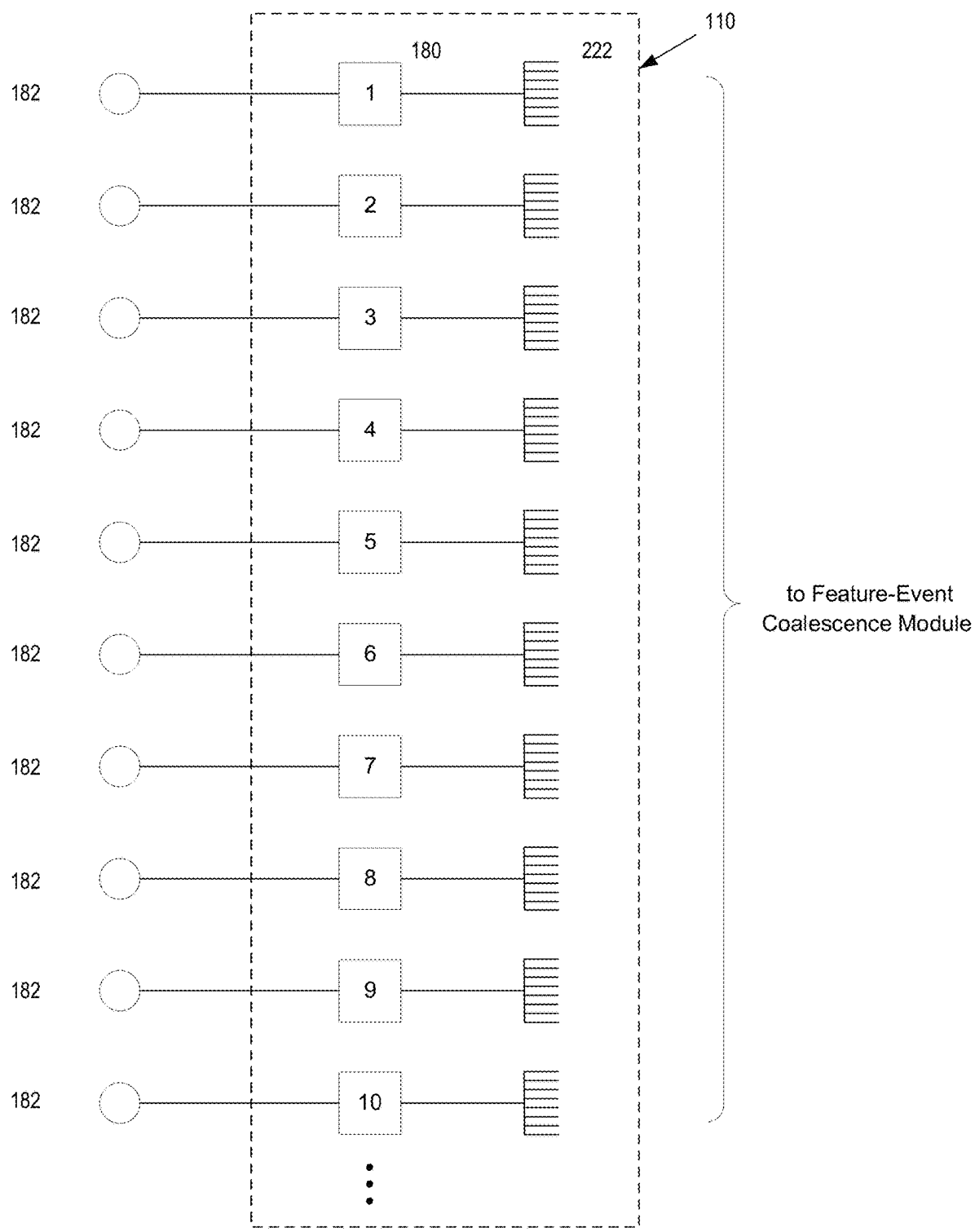
FIG. 6 illustrates a schematic of a parallel array of discrete event detectors configured to detect a plurality of discrete events from the firing of a plurality of neurons, in accordance with some embodiments.

FIG. 6 illustrates a schematic of a highly parallel array of discrete event detectors configured to detect a plurality of discrete events from the firing of a plurality of neurons, in accordance with some embodiments. Referring to FIG. 6, a plurality of neural signals may be detected using a plurality of electrodes 182 implanted in neural tissue. The plurality of electrodes may be part of a neural interface probe. The neural signals may be indicative of extracellular membrane potentials or intracellular membrane potentials. The plurality of electrodes may be electronically connected to a plurality of discrete event detectors 180. The plurality of discrete event detectors may be included as part of a feature extraction module. The plurality of discrete event detectors may be identical. In some alternative embodiments, two or more of the discrete event detectors may be different. The discrete events recorded by the plurality of discrete event detectors may be transmitted via a plurality of signal lines 222. The discrete events may be transmitted via the plurality of signal lines to a feature-event coalescence module. The plurality of discrete event detectors may be implemented in parallel using CMOS technology, or any other electronic circuit topologies or semiconductor fabrication technologies.

As previously described, the feature extraction module can be configured to perform a first step of a signal compression process, by transmitting only signals that correspond to features of the neural signals received from the electrodes. Accordingly, the amount of information required to form a representation of a given neural waveform may be reduced by a factor of 10-1000 compared to the data rate/data size imposed by the Nyquist criterion. The output from the feature extraction module is then input to the feature-event coalescence module.

Figure 7:
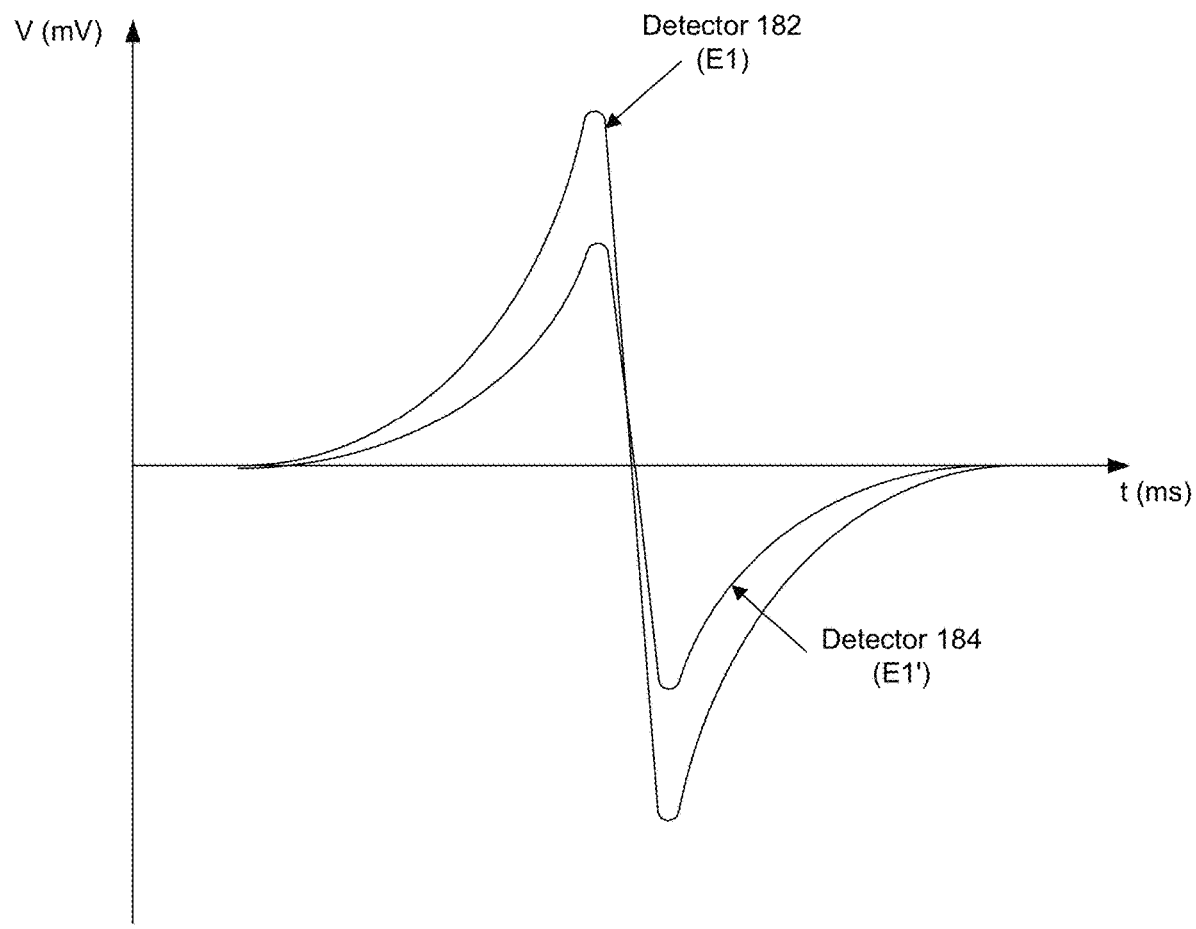
FIG. 7 illustrates neural signal waveforms obtained by two different detectors at two different locations within neural tissue, in accordance with some embodiments.

FIG. 7 illustrates neural signal waveforms obtained by two different discrete event detectors at two different locations within neural tissue, in accordance with some embodiments. Two or more different discrete event detectors may be sensitive to the firing of a single neuron, due to the physical proximity of the detectors to the neuron. In some instances, two or more different discrete event detectors may generate responses to a single neuron firing at a point in time. Each discrete event detector may detect a set of discrete events associated with the neural signal. For instance, a first detector 182 may detect the set of events {s1, s2, s3, s4, s5, s6, s7}, as previously discussed in part B of FIG. 2. This set of events {s1, s2, s3, s4, s5, s6, s7} may represent the firing of a neuron as detected by the first detector 182.

Similarly, a second detector 184 may detect a set of events {s8, s9, s10, s11, s12, s13, s14} concerning neural signal values, first time derivatives, time integrals, and timings between events, as well as additional events associated with second or higher order time derivatives and other discrete events, as measured by the second detector. The two sets of events {s1, s2, s3, s4, s5, s6, s7} and {s8, s9, s10, s11, s12, s13, s14}, as well as any additional discrete events corresponding to higher order time derivatives or any other property of interest, may then be transmitted from the first and second detectors to the feature-event coalescence module.

Figure 8:
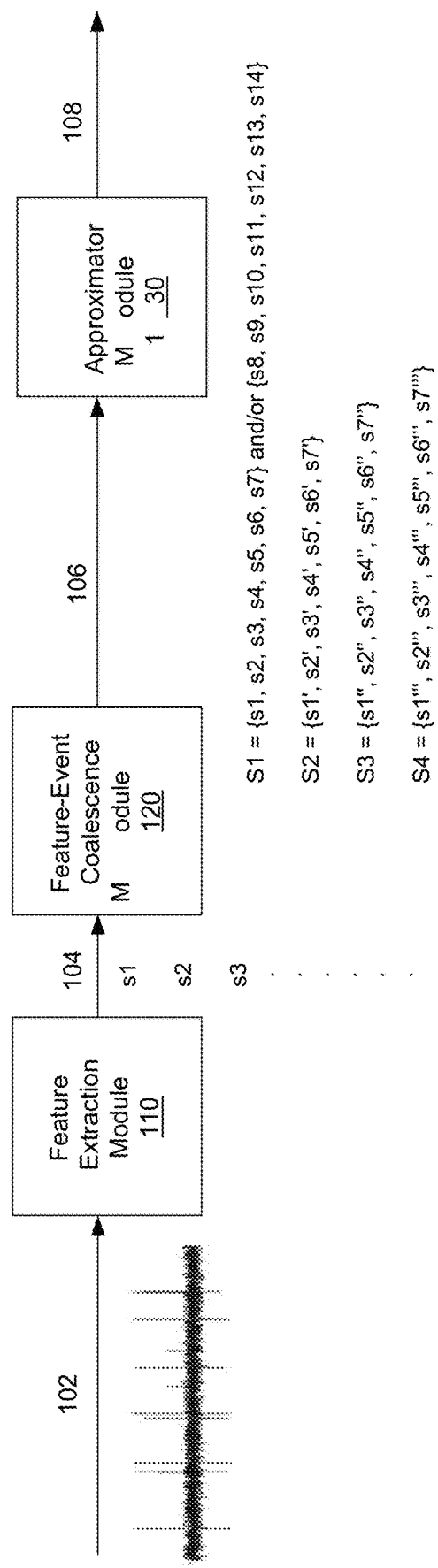
FIG. 8 illustrates the flow and processing of information by the neural data analysis system of FIG. 1, in accordance with some embodiments.

FIG. 8 illustrates the flow and processing of information in the neural data analysis system of FIG. 1, in accordance with some embodiments. As discussed in FIG. 1, neural information 102 is processed by the feature extraction module 110 to extract a set of discrete events 104. The set of discrete events may comprise {s1, s2, s3, s4, s5, s6, s7}, {s8, s9, s10, s11, s12, s13, s14}, {s1', s2', s3', s4', s5', s6', s7'}, {s1", s2", s3", s4", s5", s6", s7"}, {s1''', s2''', s3''', s4''', s5''', s6''', s7'''}, and so forth. Alternatively, the set of discrete events may comprise any other events which may be useful in the analysis of neural information.

Referring to FIG. 8, the set of discrete events 104 may be transmitted to the feature-event coalescence module 120, where it is further processed to generate a set of coalesced events 106. The feature-event coalescence module may be configured to coalesce the discrete events into one or more coalesced events. For example, the feature-event coalescence module may coalesce the set of discrete events {s1, s2, s3, s4, s5, s6, s7} into a single coalesced event S1 that is representative of the firing of a first neuron. In some cases, as previously described, the firing of the first neuron may be detected by another discrete event detector that extracts the set of events {s8, s9, s10, s11, s12, s13, s14}. Referring back to FIG. 7, the set of discrete events {s1, s2, s3, s4, s5, s6, s7} may be extracted by a first detector and associated with the waveform E1, and the set of discrete events {s8, s9, s10, s11, s12, s13, s14} may be extracted by a second detector and associated with the waveform E1'. However, both sets of discrete events {s1, s2, s3, s4, s5, s6, s7} and {s8, s9, s10, s11, s12, s13, s14} are associated with the firing of the same neuron, except they are detected using detectors that are located at different proximities to that neuron. As such, the single coalesced event S1 may be represented by either set of discrete events, or both sets of discrete events. In some embodiments, a single coalesced event may be represented by multiple sets of discrete events detected using different detectors located at different proximities to the same neuron.

As shown in FIG. 8, the feature-event coalescence module may also coalesce the set of discrete events {s1', s2', s3', s4', s5', s6', s7'} into a single coalesced event S2 that is representative of the firing of a second neuron. The set of discrete events {s1', s2', s3', s4', s5', s6', s7'} may be associated with the waveform E2 shown in FIG. 3. Similarly, the feature-event coalescence module may also coalesce the set of discrete events {s1", s2", s3", s4", s5", s6", s7"} into a single coalesced event S3 that is representative of the firing of a third neuron. The set of discrete events {s1", s2", s3", s4", s5", s6", s7"} may be associated with the waveform E3 shown in FIG. 3. Likewise, the feature-event coalescence module may coalesce the set of discrete events {s1''', s2''', s3''', s4', s5''', s6''', s7'''} into a single coalesced event S4 that is representative of the firing of a fourth neuron. The set of discrete events {s1''', s2''', s3''', s4', s5''', s6''', sT'''} may be associated with the waveform E4 shown in FIG. 3. Using the above method, the information output from the feature extraction module can be greatly compressed.

As previously described, the feature-event coalescence module may be configured to coalesce sets of discrete events from a single event discrete detector, or coalesce subsets of discrete events from within a single channel of a detector. Similarly, the feature-event coalescence module may be configured to coalesce sets of discrete events from a plurality of event discrete detectors, or subsets of discrete events from across multiple channels of the plurality of detectors. The feature-event coalescence module may be configured to coalesce discrete events on the basis of information known a priori. For instance, the feature-event coalescence module may coalesce discrete events based on prior knowledge of the characteristics of neurons. The feature-event coalescence module may also coalesce discrete events based on prior knowledge of inherent response characteristics of the electronic detection circuits within the detectors or wirings. The set of coalesced events 106 is further transmitted to an approximator module 130, where the coalesced events are further processed to generate neural code 108.

As previously mentioned, the feature-event coalescence module may perform a second step of signal compression by combining discrete events into coalesced events, to further reduce the amount of information needed to describe salient features of neural signals. During this second step, the neural signals may be further compressed by a factor of 10 to 100.

The feature-event coalescence module is configured to combine discrete events into "coalesced events" based on prior knowledge about the conditions built into the pixel circuitry and about the kinds of signals that are to be recorded ("combining logic"). For example, for threshold conditions that detect the rise and fall of a voltage past a certain predetermined reference voltage, the resultant rise and fall events would be coalesced into a single rise-and-fall event where the time between the rise and the fall events would become a feature of that event.

The combining logic of fitting discrete events to a prior may exhibit both data reduction (where the same information is expressed in fewer symbols) and denoising characteristics. A discrete event detector may produce several rise or fall events in response to one true rise or fall event in the input signal. This could be due, for example, to the real world design of the condition circuitry, which may trade off on being perfectly correct for the goal of lower power consumption and/or circuit size. In the above example, the combining logic for the resultant discrete events may regard numerous rise or fall events within a short time interval as one rise or fall event, based on the prior knowledge that designers have of the condition circuit. Multiple denoised rise and fall events may be eventually merged into one rise-and-fall event.

The combining logic may incorporate priors based on knowledge of the detector circuitry, facts about neural action potential waveforms, the structure and/or fabrication of the particular neural probe being used in the interface (e.g. patterned silicon probe or microwire bundle), because one or more of the above characteristics can affect how signals are transduced into or across channels.

An example for combining logic informed by knowledge about the neural probe in use is described as follows. In a patterned silicon probe or microwire bundle probe, adjacent electrodes will often record the same bioelectric event (e.g. action potential from a single neuron), but the event will produce a different signature voltage waveform on each electrode/channel. The combining logic in this case may choose to coalesce the simple events detected across several channels into one event, reflecting this characteristic.

An important design criterion for the combined feature extraction module and the feature-event coalescence module is that clustering analysis (such as k-means clustering, Gaussian mixture modeling, support vector machines, self-organizing maps, spectral clustering, linear discriminant analysis, logistical regression, or any other clustering analysis) on the resulting event-based data should yield similar clusters to clustering analysis to the raw input data after it has been subjected to standard feature extraction in silico (e.g. wavelet transformation, principle component analysis). The above comparison supports the conclusion that the combined feature extraction module and the feature-event coalescence module retain the information needed for the neural activity decoding task.

In some embodiments, the digital signal from the ROIC or other instantiation of the feature extraction module is transmitted out of the body using a low-energy wavelength of electromagnetic radiation that is compatible with transmission through a few millimeters or a few centimeters (e.g 1-4 mm) of biological tissue. Examples may include 60 GHz transceivers or VCSEL-based infrared transceivers. This can minimize the computation within the body, since the feature-event coalescence module and the approximator module are located outside of the body. Accordingly, heat dissipation caused by computation can be reduced within the body. In the above example, the feature-event coalescence module may be implemented via GPGPU or CPU processing.

In some alternative embodiments, where transmission bandwidth is limited and/or data rate is more important than heat dissipation, both the feature extraction module and the feature-event coalescence modules may be disposed within the body. In the above example, the feature-event coalescence module may be implemented in an ASIC or an FPGA.

In the approximator module, a new representation for the neural event data is found where the new representation has characteristics such as low dimensionality, sparse coding, and/or invariance to certain noise or signal transformations. For example, the approximator may find representations that are insensitive (or less sensitive) to signal transformations that occur when the neural interface probe moves relative to signal sources, which may occur due to cardiac or respiratory coupled movement, injury related tissue edema (swelling), or any other source of mild mechanical disturbance. With a neural probe that provides brain stimulation in addition to sensing, the exposed metal of the probe undergoes electrochemical degradation over time. This effect can be accounted for by the approximator module. Another effect that might be accounted for by the approximator module is fouling of the probe, where biological structures such as scar tissue formation and gliosis alter the electrical recording properties of the probe. The key is that in each of the above cases, a deterministic transformation is applied to the incoming neural data, and depending on the representational scheme selected by the approximator, these transformations may or may not result in a change in the output of the neural data pipeline. By training the approximator to respond invariantly in the face of predictable and deterministic perturbations to its input, these low-level changes can be made invisible to the high-level output of the pipeline.

The approximator module is configured to: 1) further reduce the total bandwidth of the signal with the goal of reducing the computational load on downstream decoders which map the neural event data to functional variables; 2) using regression methods or neural networks, find a representation or latent variable system of the percepts or movements encoded in the neural activity of various regions of the brain; and 3) in doing so, learn features which may improve downstream decoder performance.

The above objectives can be achieved by applying one or more machine learning methods that decompose their input according to a self-learned (unsupervised) set of bases, while incorporating certain constraints or priors in said decomposition. Some of the constraints used may include constraints which are aware of facts about the underlying general neural state space, such as that the neural state should not change appreciably on the sub-millisecond scale, as well as facts about the specific neural state space as may be relevant for the decoding application, such as that the primary motor cortex may encode movement in which forces are applied smoothly and do not result in a jerky motion.

The approximator module can also be implemented by explicitly modeling the data stream using probabilistic graphical models, Bayesian decoding, dynamical systems, population vector analysis, or eigendecomposition of binned firing rates. The approximator module can be implemented using matrix methods such as L1/L2 regularization (for finding sparse solutions) or eigenvector based approaches to find low rank approximations of the matrix. Regularization can be applied to all regression or objective function-based frameworks. The approximator module can also be implemented using neural networks such as autoencoders, stacked autoencoders, denoising autoencoders, deep belief networks, long short term memory networks, or any other neural network or machine learning method.

In the preferred embodiment, the approximation stage is implemented as a multi-layered neural network. This would include so-called "deep belief networks", "stacked autoencoders", recurrent neural networks, and long short term memory networks. The inner layers may be constrained by means of limiting what values their weights may take, or by limiting how quickly or tightly their weights may settle towards the optimum as a form of a regularization strategy, etc. The multiple inner layers lead to increasing degrees of abstraction and invariance to small perturbations of the signal. The input layer may be corrupted or transformed in such a manner as to favor invariant representation or denoising. The layers can be updated separately, allowing for changes in spike waveforms over time to be learned by retraining of an upstream layer while the outputs of the downstream layers remain the same.

The training phase to determine the parameters for the algorithm implemented at this stage will occur offline, but use of the approximator will be in real time. Updating of weights/coefficients may then occur regularly and while the approximator is in use.

Figure 9:
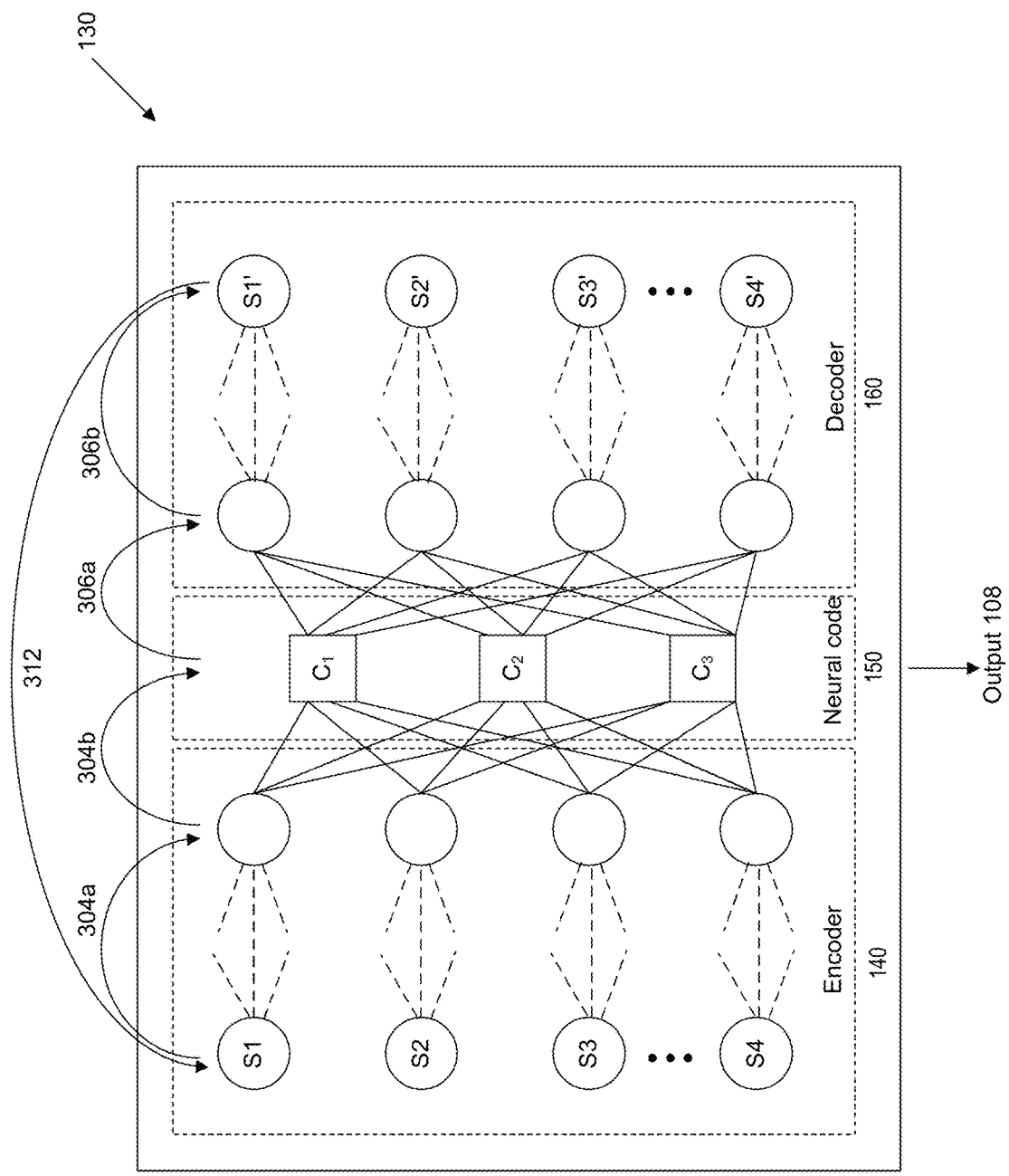
FIG. 9 illustrates an exemplary multi-layer autoencoder configured to convert a set of coalesced events from the feature-event coalescence module into a neural code, in accordance with some embodiments.

FIG. 9 illustrates an exemplary multi-layer autoencoder configured to convert a set of coalesced events from the feature-event coalescence module into a neural code, in accordance with some embodiments. Referring to FIG. 9, the approximator module 130 may comprise an encoder 140 and a decoder 160. The approximator module may be configured to output neural code 150.

In some embodiments, the encoder may further comprise a plurality of encoding layers. Each encoding layer may comprise a plurality of nodes bearing a plurality of numerical weights. Similarly, the decoder may further comprise a plurality of decoding layers. Each decoding layer may comprise a plurality of nodes bearing a plurality of numerical weights. The most constricted layer of the approximator module may represent a compressed representation of the neural code. The neural code may comprise a plurality of nodes bearing numerical weights. The neural code may specify an abstract yet meaningful representation of coalesced events within the machine learning architecture shown. In some embodiments, the approximator module may comprise an autoencoder, such that the output of the decoder is trained to be nearly identical to and provided as the input to the encoder. Following training, the decoder section of the autoencoder may be removed. The output of the most-constricted layer may be a compressed representation of the neural code. Alternatively, the decoder section of the autoencoder may be retained, such as for training and diagnostic purposes. The intermediate layer may be used to generate the output of the approximator. In some embodiments, the autoencoder may be a multi-layer autoencoder.

The encoder may be configured to receive an input comprising the set of coalesced events 106 from the feature-event coalescence module. The set of coalesced events may comprise the events S1, S2, S3, and S4 as described elsewhere herein. The set of coalesced events may be arranged as a vector S. The first layer of the encoder may be configured to reduce the dimensionality of the set of coalesced events by applying a transformation to the vector S. In some embodiments, the transformation may be a linear transformation. The transformation may produce an output vector T having reduced dimensionality relative to the vector S, based on a function G, a matrix W of weights at each node in the layer, and another vector b:

$$T = \sigma(WS+b) \quad \text{(Equation 1)}$$

The vector T is then input to the second layer. Each successive encoding layer may apply matrix transformations of the same form as Equation (1), with a successive reduction in dimensionality at each layer until the innermost layer (the neural code) is reached.

The decoder may be configured to undo the abovementioned reduction in dimensionality in order to calculate the accuracy of the matrices of weights applied at each layer of the encoder. The neural code may be input to the first layer of the decoder, which may apply a linear transformation to increase dimensionality. Each successive decoding layer may apply further matrix transformations, until an output S' from the encoding layer of the same dimensionality as the original input set S is reached.

The initial weights of each node in each layer of the encoder, decoder, and neural code may be selected based on any predetermined procedures. The series of matrix transformations may be applied to map the input S at the first encoding layer to the output S' at the final decoding layer. An objective function, such as an L1 error or an L2 error, may be calculated from S and S'. An algorithm, such as backpropagation, may then be applied to update the weights at each node in each layer of the encoder, decoder, and neural code. The algorithm may be applied iteratively until the objective function assessed at the output of the decoder reaches a minimum value.

In some embodiments, sparsity constraints may be applied on some or all of the layers in the approximator module. Other machine learning techniques including various supervised machine learning techniques, various semi-supervised machine learning techniques, and/or various unsupervised machine learning techniques can also be implemented in the approximator module.

The approximator module may be configured to distill a dataset having high dimensionality into a minimal set of numerical values that still maintains the essential features of the dataset without redundancy. This set of numerical values then forms the neural code corresponding to a given set of coalesced events. The neural code can be used to control brain-machine interface devices, which may require instruction signals of lower complexity and bandwidth.

Conventional decoding models are based on the number of action potentials (events) over a time window of 10-20 ms, so-called "firing rate models". In contrast, the system described herein can provide precise (1 ms) event times (or time periods) as an input to the autoencoder. As such, the system described herein is sensitive to the precise relative timing of action potentials which is known to encode information in many sensory systems.

In some embodiments, the autoencoder can be designed in multiple layers in order to improve its robustness against changes in the electrodes and electrode localization. This also allows specific layers to be retrained in isolation to reduce the computational overhead of adapting the system to changing recording conditions (e.g., physical changes to or variations in the electrodes).

Accordingly, the neural data analysis system described herein can serve as a pipeline for processing neural data comprising voltage waveforms from thousands, tens of thousands, hundreds of thousands, or millions of cells measured via a massively parallel electrode array. The system can transform the voltage/time data to a higher-level symbol stream which serves as the input to different types of neural decoder. The system is aligned with recent advances in neural engineering hardware, which typically exhibit a high number of channels of information that existing neural decoders often are incapable of handling.

Figure 10:
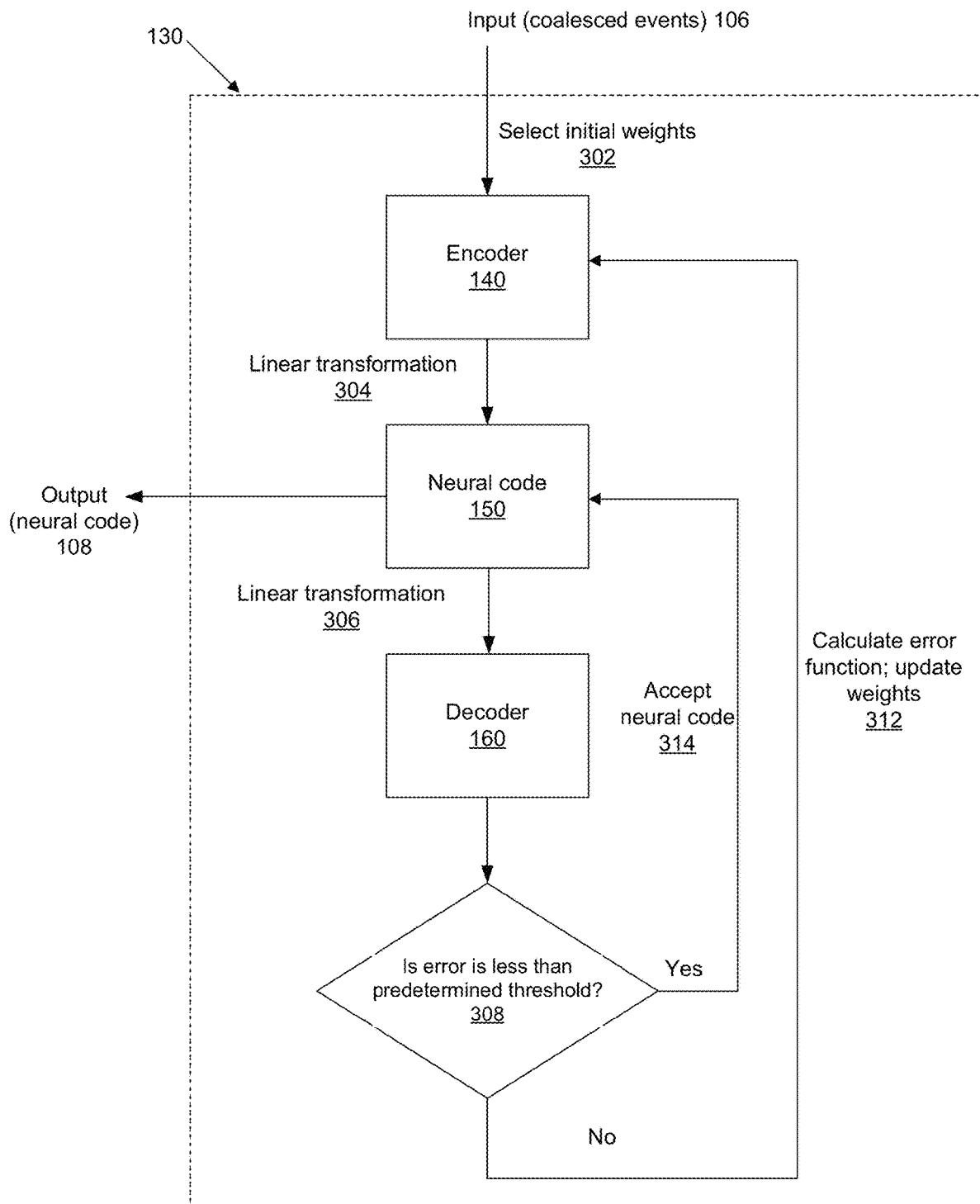
FIG. 10 illustrates a flowchart representing a process by which neural code may be extracted from the input to an autoencoder, in accordance with some embodiments.

FIG. 10 illustrates a flowchart representing a process by which neural code may be extracted from the input to an autoencoder, in accordance with some embodiments. The encoder 140 (of FIG. 9) may accept as input a vectorized set of coalesced events 106 from the feature-event coalescence module 130 (see FIG. 1). The initial weights 302 of each node in each layer of the encoder 140, neural code 150, and decoder 160 may be selected according to any preferred procedure. The encoder may apply a set of linear transformations 304, one linear transformation at each encoding layer, to calculate a first-pass linear neural code 150. Each linear transformation at each layer of the encoder may act to reduce the dimensionality of the information passed to the next layer of the encoder.

The decoder may act to apply a further set of linear transformations 306, one linear transformation at each decoding layer. Each linear transformation at each layer of the decoder may act to increase the dimensionality of the information passed to the next layer of the decoder. The final layer of the decoder may produce an output given by the weights of the nodes of the final layer of the decoder. The output may be of the same dimensionality as the input to the decoder 106. Though described as linear with respect to FIG. 3, one or more transformations may be non-linear transformations.

The values of the output and the values of the input to the encoder 106 may be compared through an objective function in order to calculate an error. The objective function may be the L1 error, given by the sum of absolute differences between the output and the input to the encoder 106. For supervised training, the error may be the error between the output layer and target data (such as labeled data) for the respective input. The objective function may be the L2 error or the Euclidean error, given by the sum of the squared differences between the output and the input to the encoder 106. The objective function may be an LN error, or a generalized p-norm error of arbitrary dimensionality N. The objective function may be any other objective function. The objective function may include, for example, a Kullback-Leibler divergence term, a cross entropy term, a logistic loss term, a hinge loss term, or any other cost or loss function term. The objective function may be the same for each iteration. The objective function may change between successive iterations. The objective function may include a regularization term, such as an L1 or L2 regularization. The objective function may be a combination of any of these example objective functions or other expressions. The objective function may include hyperparameters to dynamically control the proportion of error and regularization in the objected function. The hyperparameters may be controlled via Bayesian regularization or any other procedure.

The error calculated from the output and the input to the encoder 106 may be compared to a condition. The condition may be based on a predetermined threshold. If the error satisfies the condition, the neural code may be accepted 314 and the value of the neural code may be output 108. If the error fails to satisfy the condition, the weights of each node in each layer of the encoder 140, neural code 150, and decoder 160 may be updated 314 according to any preferred procedure. At this point, the procedure may proceed iteratively until the condition is satisfied. The condition may be defined such that that the error is smaller than a predetermined threshold value. The condition may also be defined such that the error is the smaller than any of previously calculated errors. In some embodiments, the condition may remain the same for each iteration. In other embodiments, the condition may change between successive iterations. The procedure and iterations may be configured to end when the condition is met. In some embodiments, when the condition is met, the neural code from the current iteration will be output to external equipment. As previously mentioned, the external equipment may include devices such as speech synthesizers or prosthetics.

Figure 11:
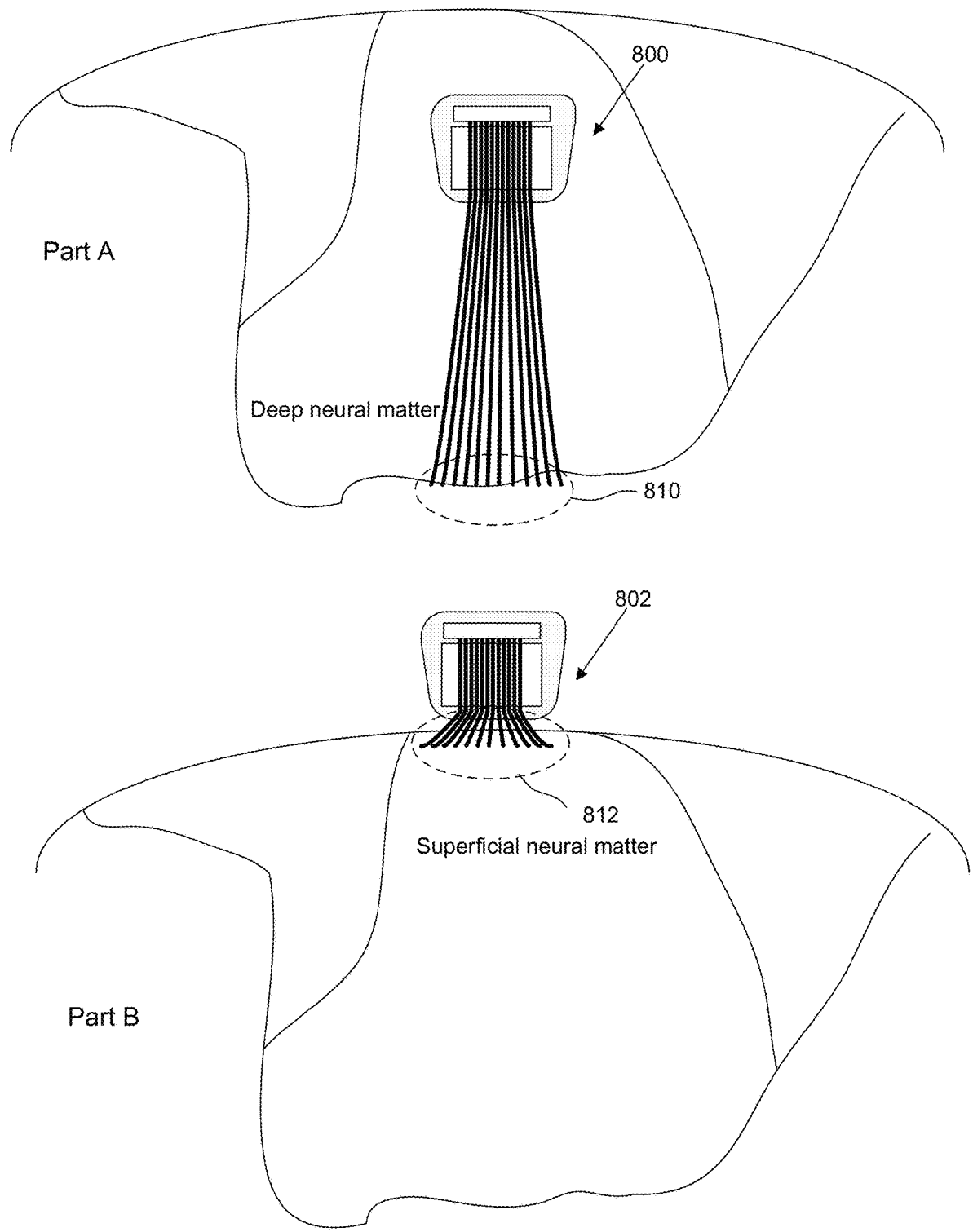
FIG. 11 illustrates examples of neural-interface probes being implanted in different regions of a human brain, in accordance with some embodiments.

FIG. 11 illustrates examples of neural-interface probes being implanted in different regions in a brain, in accordance with some embodiments. Part A of FIG. 11 depicts a schematic of a neural-interface probe 800 implanted deep within a brain, in accordance with some embodiments. The probe 800 may be inserted into the deep-tissue regions of the brain of a test subject. During insertion of the probe, the free ends of the wires spread out within the brain tissue such that the electrodes deploy in a three-dimensional arrangement over a deep-brain target area 810. Part B of FIG. 11 depicts a schematic of a neural-interface probe 802 implanted on a superficial target on a brain, in accordance with some embodiments. The probe may be inserted onto a superficial tissue region 812 of the brain of a test subject. The tissue region may, for example be a cortical region of the brain. When the probe 802 is implanted on the tissue region 812, the free ends of the wires spread out such that the electrodes deploy in a three-dimensional arrangement over the tissue region 812. The system may also be configured to be implanted in regions of the peripheral nervous system, such as the spinal cord.

Comparing parts A and B of FIG. 11, it may be observed that the neural-interface probe 800 has a high aspect ratio since it is used in deep brain regions, whereas the neural-interface probe 802 has a low aspect ratio since it is used in shallow or superficial brain regions. In some embodiments, a length of a neural-interface probe may range from about 1 cm to about 8 cm. Accordingly, neural-interface probes of different lengths and other dimensions (width, etc.) may be used for different regions of the brain in accordance with various embodiments of the invention. The probes can be used to implement a method for monitoring and/or stimulating neural activity. In some embodiments, the method may comprise inserting the probe into a brain, such that the flexible distal portion of the wires interfaces and is in contact with an area of the neural matter. The method may further comprise monitoring and/or stimulating neural activity in the area via a plurality of electrical signals transmitted between the chip and the neural matter. The plurality of electrical signals may be transmitted through the plurality of wires. In some embodiments, the method may further comprise transmitting the electrical signals from the probe to the neural data analysis system described herein, via one or more wireless or wired communication channels.

In some embodiments, the implanted neural-interface probes may be connected to the external world via a percutaneous wire. The percutaneous wire may be inserted through a patient's scalp. In other embodiments, the implanted neural-interface probes may be connected to the external world via a wireless telemetry unit.

Figure 12:
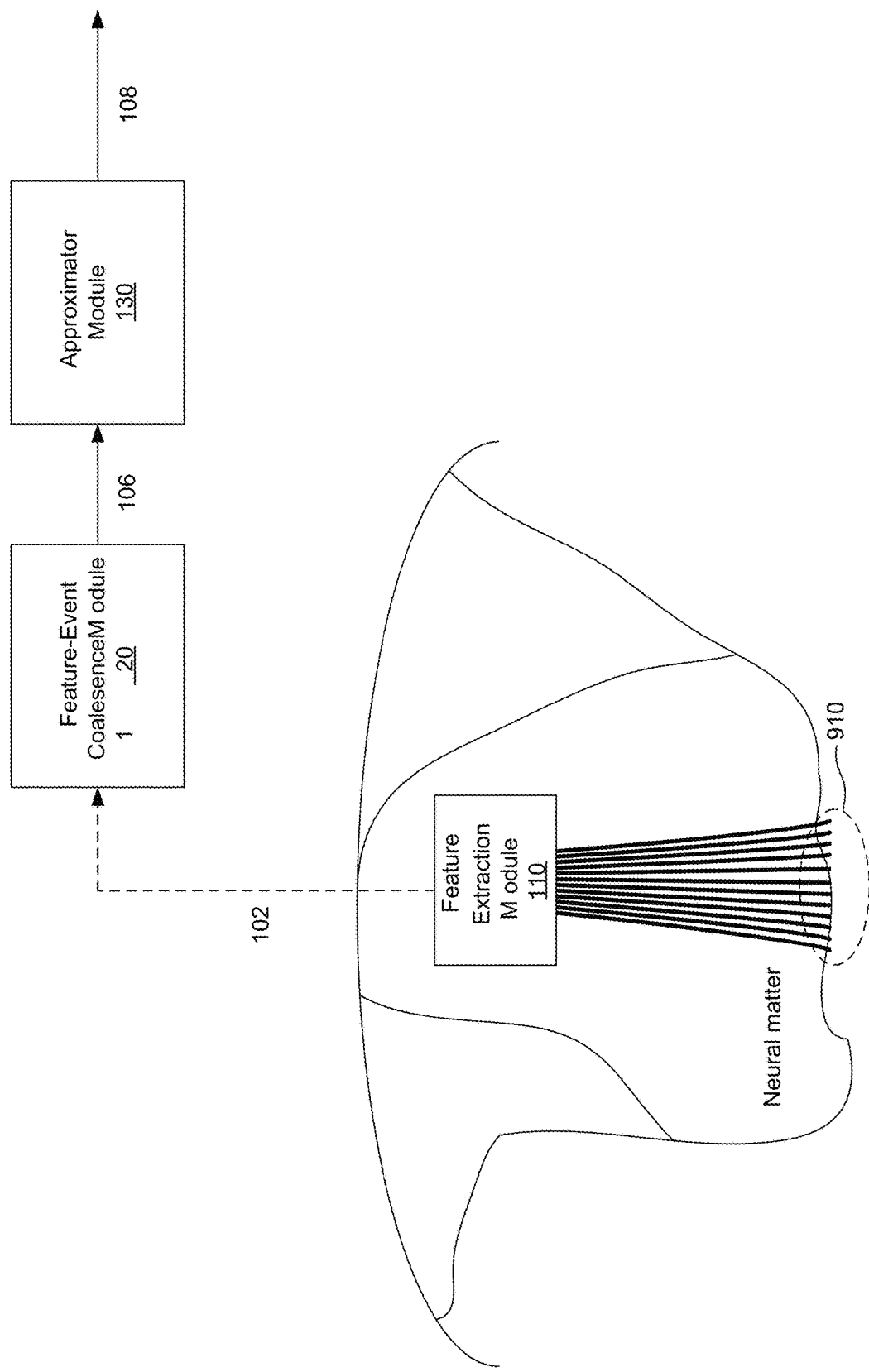
FIG. 12 illustrates the flow of information from an implanted neural interface probe to one or more components of an exemplary neural data analysis system located outside of the human body, in accordance with some embodiments.

FIG. 12 illustrates the flow of information from an implanted neural interface probe to one or more components of an exemplary neural data analysis system located outside of the human body, in accordance with some embodiments. In FIG. 12, the feature extraction module 110 may be included as part of the neural interface probe shown in FIG. 11.

The feature extraction module may receive neural signals from a plurality of wires or microelectrodes which have been implanted into deep neural matter or superficial neural matter. As such, the feature extraction module may itself be implanted into neural matter. The feature extraction module may be configured to transmit sets of discrete events to the feature-event coalescence module 120. The feature-event coalescence module may be located outside of the human body. In some embodiments, the feature extraction module may transmit the sets of discrete events wirelessly to the feature-event coalescence module. The data transmission may be via microwave transmission, via IR optical means such as VCSEL arrays, or via other wireless technologies. The transmission may be via ultra-wideband (UWB) transmission. The transmission may be a wired transmission, such as by a percutaneous lead. The percutaneous lead may carry neural signals from the electrodes to a location outside the body, such as a subject's chest. The feature-event coalescence module and the approximator module may be implemented using one or more processors on a CPU or a GPGPU.

In some embodiments, the digital signal from the feature extraction module is transmitted out of the body using a low-energy wavelength of electromagnetic radiation that is compatible with transmission through 1-4 mm of tissue. Examples of such transceivers may include 60 GHz transceivers or VCSEL-based infrared transceivers. The transceiver may be an ultra-wideband (UWB) transceiver. Alternatively, signals may be transmitted by a wired transmission, such as by a percutaneous lead. The percutaneous lead may carry neural signals from the electrodes to a location outside the body, such as a subject's chest. This minimizes the amount of computation to be performed within the body. Therefore heat dissipation from the one or more processors within the body is reduced. In these embodiments, the feature-event coalescence module may be implemented in a GPGPU or CPU.

In some alternative embodiments, where transmission bandwidth is limited and/or data rate is more important than heat dissipation, both the feature extraction module and feature-event coalescence module may be implanted within the body. In these embodiments, the feature-event coalescence module may be implemented in an ASIC or a FPGA.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A neural data analysis system comprising:
    an implantable neural interface probe configured to collect neural signal waveforms, wherein the neural interface probe comprises a massively parallel electrode array, wherein the massively parallel electrode array comprises a plurality of microelectrodes bonded to a readout integrated circuit (ROIC), and wherein the ROIC comprises a plurality of sensing pixels;
    a feature extraction module comprising one or more low-power, mixed-signal integrated circuits, wherein the feature extraction module is configured to (1) extract a plurality of features from the neural signal waveforms without requiring prior digitization of the neural signal waveforms, and (2) transmit the extracted features as a plurality of discrete outputs;
    a feature-event coalescence module configured to (1) receive the plurality of discrete outputs from the feature extraction module, (2) construct a model-based inference of bioelectric activity from the plurality of discrete outputs based in part on feature-event statistics, prior knowledge of bioelectric signals, and/or a behavioral model of the feature extraction module, wherein the model-based inference of bioelectric activity comprises a plurality of coalesced events, and each of the plurality of coalesced events comprises two or more discrete events that are coalesced; and
    an approximator module configured to (1) receive the plurality of coalesced events from the feature-event coalescence module, and (2) apply a series of transformations to the plurality of coalesced events to generate a neural code, wherein the neural code comprises a representation of ensemble activity of a plurality of neurons recorded by the system.

2. The neural data analysis system of claim 1, wherein the feature-event coalescence module is configured to perform the step of (2) without discarding one or more of the neural signal waveforms on a basis that information associated with said one or more of the neural signal waveforms is unable to be attributed to a source neuron.

3. The neural data analysis system of claim 1, wherein the feature-event coalescence module is configured to perform the step of (2) without needing to classify each of the two or more discrete events as relating to au particular neuron.

4. The neural data analysis system of claim 1, wherein distal ends of the plurality of microelectrodes are flexible and configured to contact with neural matter when the neural interface probe is implanted.

5. The neural data analysis system of claim 1, wherein the neural signal waveforms are extracellular or intracellular action potential waveforms.

6. The neural data analysis system of claim 1, wherein the plurality of microelectrodes are bonded to the plurality of sensing pixels to form a plurality of channels.

7. The neural data analysis system of claim 6, wherein the one or more low-power, mixed-signal integrated circuits are configured to transmit the plurality of features by either:
    (a) sampling the neural signal waveforms based on a set of predetermined trigger conditions and transmitting one or more analog or digital values, or
    (b) transmitting one or more binary pulses marking a presence of one or more trigger conditions from the set of predetermined trigger conditions.

8. The neural data analysis system of claim 7, wherein the set of predetermined trigger conditions comprises at least one of the following: (1) a voltage magnitude of a neural signal waveform meeting, exceeding, or falling below a first threshold value; (2) a derivative of the neural signal waveform meeting, exceeding, or falling below a second threshold value; (3) an integral of the neural signal waveform meeting, exceeding, or falling below a third threshold value; (4) a ratiometric criterion; or (5) the neural signal waveform reaching a local maximum value or a local minimum value.

9. The neural data analysis system of claim 8, wherein the integral of the neural signal waveform is obtained using a leaky integrator of the system.

10. The neural data analysis system of claim 8, wherein the ratiometric criterion includes a comparison of relative power between two or more frequency bands within the neural signal waveform.

11. The neural system of claim 8, wherein the feature extraction module is configured to produces a plurality of parallel transformations of the neural signal waveform.

12. The neural system of claim 11, wherein one or more sampling circuits in the feature extraction module are configured to extract the plurality of features by sampling (a) the neural signal waveform or (b) one or more transformations of the neural signal waveform, based on one or more triggering conditions detected on another neural signal waveform.

13. The neural data analysis system of claim 12, wherein a time duration between (i) detection of the one or more triggering conditions and (ii) transmission of one or more of the plurality of features has a fixed delay between zero and ten milliseconds.

14. The neural data analysis system of claim 1, wherein the one or more low-power, mixed-signal integrated circuits comprise one or more analog circuits and low-resolution analog-to-digital converters.

15. The neural data analysis system of claim 1, wherein the one or more low-power, mixed-signal integrated circuits are configured to implement one or more analog transformation operations on the neural signal waveforms.

16. The neural data analysis system of claim 15, wherein the one or more analog transformation operations transform the neural signal waveforms using a plurality of transfer functions which constitute a basis set for spectral decomposition.

17. The neural data analysis system of claim 16, wherein the basis set comprises a plurality of eigenvectors or a wavelet basis set.

18. The neural data analysis system of claim 1, wherein the feature-event coalescence module is configured to reconstruct the plurality of coalesced events based on a plurality of subsets of the extracted features.

19. The neural data analysis system of claim 1, wherein the feature-event coalescence module is configured to identify and merge two or more of the plurality of features into a single coalesced event.

20. The neural data analysis system of claim 19, wherein the plurality of features are extracted based on one or more threshold conditions being met when a voltage level, time derivative of a voltage level, or time integral of voltage level of the neural signal waveforms rises or falls relative to one or more predetermined reference voltages.

21. The neural data analysis system of claim 20, wherein the model-based inference of bioelectric activity is further constructed based on one or more of the following: (1) characteristic(s) of electronic circuits that are used in the feature extraction module; (2) type, structure, and/or fabrication process of the neural interface probe; (3) transmission of the neural signal waveforms across multiple channels of the probe and the feature extraction module; or (4) locations of adjacent electrodes of the neural interface probe relative to one or more neurons.

22. The neural data analysis system of claim 19, wherein the feature-event coalescence module is configured to account for temporal dynamics that distinguish action potentials originating from different sources, by merging the two or more of the plurality of features into the single coalesced event with identifying information about the temporal dynamics.

23. The neural data analysis system of claim 1, wherein the representations of the ensemble activity of the plurality of neurons comprises one or more of the following characteristics: (1) low dimensionality; (2) sparse coding; and (3) invariance to noise or signal transformations.

24. A neural data analysis system comprising:
a feature extraction module comprising one or more low-power, mixed-signal integrated circuits, wherein the feature extraction module is configured to (1) extract a plurality of features from neural signal waveforms without requiring prior digitization of the neural signal waveforms, and (2) transmit the extracted features as a plurality of discrete outputs, wherein the one or more low-power, mixed-signal integrated circuits are configured to extract and transmit the plurality of features by either:
(a) sampling the neural signal waveforms based on a set of predetermined trigger conditions and transmitting one or more analog or digital values, or
(b) transmitting one or more binary pulses marking a presence of one or more trigger conditions from the set of predetermined trigger conditions,
wherein the set of predetermined trigger conditions comprises at least one of the following: (1) a voltage magnitude of a neural signal waveform meeting, exceeding, or falling below a first threshold value; (2) a derivative of the neural signal waveform meeting, exceeding, or falling below a second threshold value; (3) an integral of the neural signal waveform meeting, exceeding, or falling below a third threshold value; (4) a ratiometric criterion that includes a comparison of relative power between two or more frequency bands within the neural signal waveform; or (5) the neural signal waveform reaching a local maximum value or a local minimum value;
a feature-event coalescence module configured to (1) receive the plurality of discrete outputs from the feature extraction module, (2) construct a model-based inference of bioelectric activity from the plurality of discrete outputs based in part on feature-event statistics, prior knowledge of bioelectric signals, and/or a behavioral model of the feature extraction module, wherein the model-based inference of bioelectric activity comprises a plurality of coalesced events, and each of the plurality of coalesced events comprises two or more discrete events that are coalesced; and
an approximator module configured to (1) receive the plurality of coalesced events from the feature-event coalescence module, and (2) apply a series of transformations to the plurality of coalesced events to generate a neural code, wherein the neural code comprises a representation of ensemble activity of a plurality of neurons recorded by the system.

25. A neural data analysis system comprising:
a feature extraction module comprising one or more low-power, mixed-signal integrated circuits, wherein the feature extraction module is configured to (1) produce a plurality of parallel transformations of a neural signal waveform, (2) extract a plurality of features from the neural signal waveform without requiring prior digitization of the neural signal waveform, wherein the plurality of features are extracted by sampling one or more transformations of the plurality of parallel transformations, based on one or more triggering conditions detected on another neural signal waveform, and (3) transmit the extracted features as a plurality of discrete outputs,
wherein the one or more triggering conditions are from a set of predetermined trigger conditions comprising at least one of the following: (1) a voltage magnitude of the neural signal waveform meeting, exceeding, or falling below a first threshold value; (2) a derivative of the neural signal waveform meeting, exceeding, or falling below a second threshold value; (3) an integral of the neural signal waveform meeting, exceeding, or falling below a third threshold value; (4) a ratiometric criterion; or (5) the neural signal waveform reaching a local maximum value or a local minimum value;

a feature-event coalescence module configured to (1) receive the plurality of discrete outputs from the feature extraction module, (2) construct a model-based inference of bioelectric activity from the plurality of discrete outputs based in part on feature-event statistics, prior knowledge of bioelectric signals, and/or a behavioral model of the feature extraction module, wherein the model-based inference of bioelectric activity comprises a plurality of coalesced events, and each of the plurality of coalesced events comprises two or more discrete events that are coalesced; and an approximator module configured to (1) receive the plurality of coalesced events from the feature-event coalescence module, and (2) apply a series of transformations to the plurality of coalesced events to generate a neural code, wherein the neural code comprises a representation of ensemble activity of a plurality of neurons recorded by the system.

\* \* \* \* \*